(12) United States Patent
Hu

(10) Patent No.: US 12,067,716 B2
(45) Date of Patent: Aug. 20, 2024

(54) OVARIAN TOXICITY ASSESSMENT IN HISTOPATHOLOGICAL IMAGES USING DEEP LEARNING

(71) Applicant: GENENTECH, INC., South San Francisco, CA (US)

(72) Inventor: Fang-Yao Hu, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 251 days.

(21) Appl. No.: 17/501,712

(22) Filed: Oct. 14, 2021

(65) Prior Publication Data
US 2022/0036548 A1    Feb. 3, 2022

Related U.S. Application Data

(63) Continuation of application No. PCT/US2020/028100, filed on Apr. 14, 2020.
(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4325* (2013.01); *A61B 5/4845* (2013.01);
(Continued)

(58) Field of Classification Search
CPC ......... G06T 7/0012; G06T 2207/30024; G06T 2207/30242; G16H 30/20; G16H 30/40;
(Continued)

(56) References Cited

U.S. PATENT DOCUMENTS

2017/0190774 A1* 7/2017 Kara .................. A61P 5/06
2020/0179308 A1* 6/2020 Bland ................. A61P 5/50
(Continued)

OTHER PUBLICATIONS

High-throughput ovarian follicle counting by an innovative deep learning approach (Charlotte Sonigo, Stéphane Jankowski, Olivier Yoo, Olivier Trassard, Nicolas Bousquet, Michael Grynberg, Isabelle Beau & Nadine Binart , 2018) (Year: 2018).*
(Continued)

*Primary Examiner* — Khai M Nguyen
(74) *Attorney, Agent, or Firm* — Kilpatrick Townsend & Stockton LLP

(57) ABSTRACT

The present disclosure relates to a deep learning neural network that can identify corpora lutea in the ovaries and a rules-based technique that can count the corpora lutea identified in the ovaries and infer an ovarian toxicity of a compound based on the count of the corpora lutea (CL). Particularly, aspects of the present disclosure are directed to obtaining a set of images of tissue slices from ovaries treated with an amount of a compound; generating, using a neural network model, the set of images with a bounding box around objects that are identified as the CL within the set of images based on coordinates predicted for the bounding box; counting the bounding boxes within the set of images to obtain a CL count for the ovaries; and determining an ovarian toxicity of the compound at the amount based on the CL count.

20 Claims, 8 Drawing Sheets

Related U.S. Application Data

(60) Provisional application No. 62/834,237, filed on Apr. 15, 2019.

(51) Int. Cl.
| | |
|---|---|
| *G06N 3/08* | (2023.01) |
| *G06V 10/25* | (2022.01) |
| *G06V 10/94* | (2022.01) |
| *G06V 20/69* | (2022.01) |
| *G16H 30/20* | (2018.01) |
| *G16H 30/40* | (2018.01) |
| *G16H 50/20* | (2018.01) |
| *G16H 50/30* | (2018.01) |
| *G16H 50/70* | (2018.01) |

(52) U.S. Cl.
CPC ............ *A61B 5/4848* (2013.01); *G06N 3/08* (2013.01); *G06V 10/25* (2022.01); *G06V 10/95* (2022.01); *G06V 20/693* (2022.01); *G16H 30/20* (2018.01); *G16H 30/40* (2018.01); *G16H 50/20* (2018.01); *G16H 50/30* (2018.01); *G16H 50/70* (2018.01); *G06T 2207/30024* (2013.01); *G06T 2207/30242* (2013.01); *G06V 2201/031* (2022.01)

(58) Field of Classification Search
CPC ........ G16H 50/30; G16H 50/70; G16H 50/20; G06V 10/25; G06V 10/95; G06V 20/693; G06V 2201/031; A61B 5/4325; A61B 5/4845; A61B 5/4848; G06N 3/08
See application file for complete search history.

(56) References Cited

U.S. PATENT DOCUMENTS

| | | | | |
|---|---|---|---|---|
| 2020/0293832 | A1* | 9/2020 | Buslaev | G06F 18/217 |
| 2021/0090694 | A1* | 3/2021 | Colley | G16H 15/00 |

OTHER PUBLICATIONS

Focal Loss for Dense Object Detection (Tsung-Yi Lin, Priya Goyal, Ross Girshick, Kaiming He, Piotr Dollár) (Year: 2017).*
Charlette Sonigo (High-throughput ovarian follicle counting by an innovative deep learning approach, Apr. 10, 2018) (Year: 2018).*
Tsung-Yi Lin (Focal loss for Dense Object Detection, 2017) (Year: 2017).*
Abadi et al. "TensorFlow : Large-Scale Machine Learning on Heterogenous Systems", Preliminary White Papter, Nov. 9, 2015, 19 pages. Accessed from: https://www.tensorflow.org/about/bib.
Bautista, et al., "Color Standardization in Whole Slide Imaging Using a Color Calibration Slide". J Pathol Inform Jan. 31, 2014, 11 pages.
Bejnordi, et al., "Stain Specific Standardization of Whole-Slide Histopathological Images". IFFE Trans Med Imaging 35(2), 404-415, Feb. 2016.
Bolon, et al., "Differential Follicle Counts as a Screen for Chemically Induced Ovarian Toxicity in Mice, Results fromContinuous breeding Bioassays". FundamAppl Toxicol 39(1), 1-10, Sep. 1997 Article No. FA972338.
Bucci et al., "Influence of sampling on the reproducibility of ovarian follicle counts in mouse toxicity studies" Reprod Toxicol. Sep.-Oct. 1997;11(5):689-696.
D'Agostino R.B., "Tests for departure fromnormality". Biometrika. Dec. 1973;60:613-622.
D'Agostino R.B., "An omnibus test of normality for moderate and large sample size". Biometrika. 1971;58:341-348, revised, Nov. 1970.
Ferlaino, et al., "Tow ards Deep Cellular Phenotyping in Placental Histology". 1st Conference in Medical Imaging with Deep Learning, May 25, 19 pages.
He, et al., "Deep Residual Learning for Image Recognition", arXiv.0rg>cs>arXiv:1512.03385, Submitted Dec. 10, 2015, 12 pages.
Hu, et al., "Ovarian Toxicity Assessment in Histopathalogical Image Using Deep Learning", Toxicol Pathol. Feb. 1, 2020, 48(2):350-361. DOI: 10.1177/0192623319877871.
Kingma et al., "A Method for Stochastic Optimization" 3rd International Conference for Learning Representations. https://arxiv.org/abs/1412.6980; Submitted Dec. 22, 2014, last revised Jan. 30, 2017, 15 pages.
Kobel, et al., "Diagnosis of Ovarian Carcinoma Cell Type is Highly Reproducible: A Transcanadian Study", Am J Surg Pathol 34(7), 984-993. Jul. 2010.
Kumazawa, et al., "Collaborative Work on Evaluation of Ovarian Toxicity. 15. Two- or four-week repeated-dose studies and fertility study of bromocriptine in female rats", J Toxicol Sci 34 Special Issue 1, SP157-165, 2009, received Dec. 10, 2008.
Lin, et al., "Focal Loss for Dense Object Detection". 2017 IEFE International Conference on Computer Vision, Oct. 22, 2017. 9 pages.
Liu, et al., "Artificial Intelligence-Based Breast Cancer Nodal Metastasis Detection", Arch Pathol Lab Med, Jul. 2019;143(7):859-868. doi: 10.5858/arpa.2018-0147-OA. Epub 2018.
Madabhushi, et al., "Image Analysis and Machine Learning in Digital Pathology", Challenges and Opportunities. Med Image Analysis 33, 170-175, Aug. 15, 2017.
Meredith, et al., "Single-section counting error w hen distinguishing between primordial and early primary follicles in sections of rat ovary of different thickness", J Reprod Fertil. Nov. 1999;117(2):339-343.
Otsu; N. "A threshold selection method from gray-level histograms" IEEE Trans Sys Man Cyber. Jan. 1979;9(1):62-66.
Regan et al., Group, "STP position paper: Ovarian Follicular Counting in the Assessment of Rodent Reproductive Toxicity", Toxicol Pathol 33(3), 409-412, Apr. 2005.
Sanbuissho, et al., "Collaborative Work on Evaluation of Ovarian Toxicity by Repeated-Dose and Fertility Studies in Female Rats", J Toxicol Sci, 2009:34 Suppl 1, SPI-22.
Sato, et al., "Comparative histopathology of the estrous or menstrual cycle in laboratory animals", J Toxicol Pathol. Jul. 2016;29(3):155-162.
Shirai, et al., "Collaborative Work on Evaluation of Ovarian Toxicity, Tw o- or Four-Week Repeated-Dose Studies and Fertility Study of Anastrozole in Female Rats", J Toxicol Sci 2009:34 Suppl 1, SP91-99.
Sonigo, et.al., "High Throughput Ovarian Follicle Counting by an Innovative Deep Learning Approach", Scientific Reports, vol. 8, No. 1, Sep. 10, 2018 (Sep. 10, 2018), XP055705206, DOI: 10.1038/s41598-018-31883-8, 9 pages.
Steiner, et al. "Impact of Deep Learning Assistance on the Histopathologic Review of Lymph Nodes for Metastatic Breast Cancer", AmJ Surg Pathol. Dec. 2018;42(12):1636-1646.
International Application No. PCT/US2020/028100 received an International Search Report and Written Opinion mailed Jul. 31, 2020, 13 pages.

\* cited by examiner

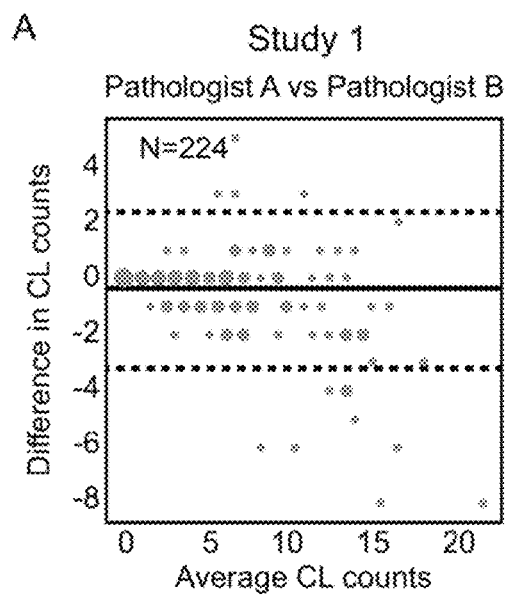
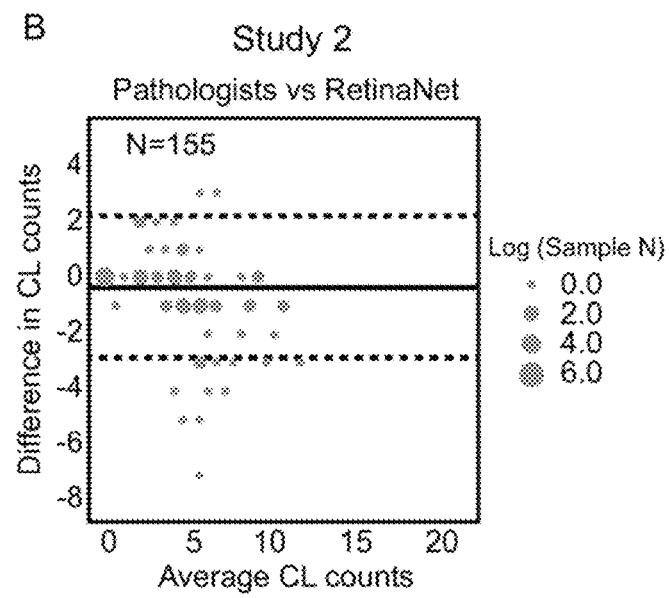
FIG. 6A  FIG. 6B
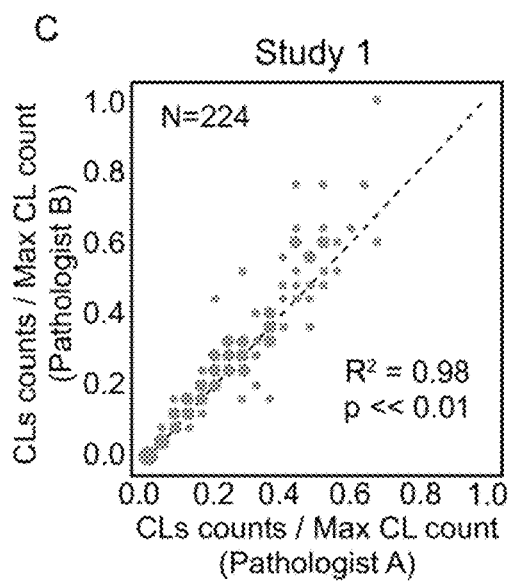
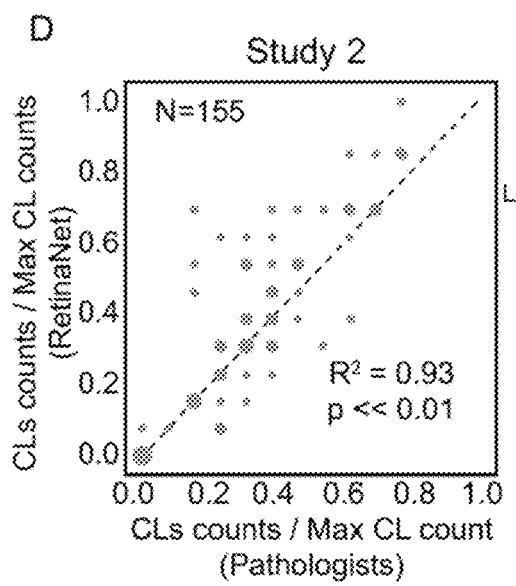
FIG. 6C  FIG. 6D

OVARIAN TOXICITY ASSESSMENT IN HISTOPATHOLOGICAL IMAGES USING DEEP LEARNING

CROSS-REFERENCE TO RELATED APPLICATIONS

The present application is a continuation application filed under 35 U.S.C. § 111(a), which claims priority to International Application PCT/US2020/028100, filed Apr. 14, 2020, which claims priority to U.S. Provisional Application No. 62/834,237, filed Apr. 15, 2019, the disclosures of which are incorporated herein by reference in their entirety for all purposes.

FIELD

The present disclosure relates to ovarian toxicity assessment, and in particular to a deep learning neural network that can identify corpora lutea in the ovaries and a rules-based technique that can count the corpora lutea identified in the ovaries and infer an ovarian toxicity of a compound based on the count of the corpora lutea.

BACKGROUND

The identification of ovarian pathology in preclinical studies is important in the general safety assessment of novel therapeutics because oocytes have no regenerative ability, and any abnormalities in the ovaries may be directly linked to impairment of female reproductive capability. The identification of ovarian pathology and provision of specific information about ovarian pathology typically includes qualitative and quantitative evaluation of follicles in the ovary. The ovary is a complicated structure and its morphology changes with the estrous cycle such that detection of impairment of ovarian function requires a complete understanding of normal ovarian morphology and variation of the ovarian morphology through the estrous cycle. In particular, the growth of follicles and their regression, as well as knowledge of the hypothalamus-pituitary-gonadal control system are indispensable for assessment of any abnormalities in the ovaries.

Primordial germ cells within the ovaries multiply during fetal development. At birth, the ovary contains thousands of primordial follicles which contain primary oocytes. These primary oocytes do not undergo further mitotic division, and they remain arrested in the prophase stage of meiotic division I, until sexual maturity. At sexual maturity, two hormones, produced by the pituitary gland: follicle stimulating hormone (FSH) and lutenising hormone (LH) cause these primordial follicles to develop. In each estrous cycle, a number of primordial follicles are activated to begin maturation. however, not all follicles fully mature, and the rest contribute to the endocrine function of the ovary. When activated, the first meiotic division is completed and the primary follicles have matured into secondary follicles. The second division then starts, and Graafian follicles are formed. The Graafian follicles contain secondary oocytes. This second division is not completed, unless the ovum is fertilized.

The development and ripening of the primordial follicles to Graafian follicles results in an increase in oestrogen levels, as oestrogen is secreted by follicular cells. This increase in oestrogen levels feeds back to the pituitary, and suppresses further release of FSH (negative feedback). The follicles also release a second hormone called inhibin, which also suppresses further production of FHS. As the oestrogen levels rise, this triggers a mid-cycle surge in LH, which causes the Graafian follicle to rupture (ovulation). LH also causes ruptured Graafian follicles to lutenise, forming a transitory endocrine organ called the corpora lutea (CL). This looks yellow, due to its pigmented lutein cells. The CL secretes progesterone and oestrogen. The progesterone levels feed back to the pituitary and suppress further release of LH. If fertilization does not occur, the CLs degenerate into a small white fibrous scar called the corpus albicans. The resulting decline in progesterone (and to some extent oestrogen) levels precipitate menstruation. The decline in oestrogen levels, feeds back to the pituitary and there is a corresponding increase in FSH to begin the estrous cycle all over again. Qualitative and quantitative follicular analysis using serial sections of the ovaries is accepted for assessment of both fertility and toxicology, although the approach is very laborious and time consuming.

SUMMARY

In various embodiments, a method is provided that includes: obtaining a set of images of tissue slices from one or more ovaries treated with an amount of a compound; inputting the set of images into a neural network model constructed as a one-stage detector using focal loss as at least a portion of the loss function; predicting, using the neural network model, coordinates for a bounding box around one or more objects within the set of images that is identified as CL; outputting, using the neural network model, the set of images with the bounding box around the one or more objects that are identified as the CL based on the coordinates predicted for the bounding box; counting the bounding boxes within the set of images output from the deep learning neural network to obtain a CL count for the ovary; and determining an ovarian toxicity of the compound at the amount based on the CL count for the ovary.

In some embodiments, the tissue slices are stained with hematoxylin and eosin (H&E).

In some embodiments, the method further includes: obtaining the tissue slices from the one or more ovaries; mounting the tissues slices on a plurality of slides; treating the plurality of slides with a hematoxylin and eosin (H&E) stain; and imaging each slide of the plurality of slides with an imaging device to generate the set of images of tissue slices.

In some embodiments, the one or more ovaries are a plurality of ovaries and the set of images comprise at least one image of a tissue slice from each ovary of the plurality of ovaries.

In some embodiments, the one or more ovaries are from one or more subjects.

In some embodiments, the neural network model is structured based on a model architecture selected from the group consisting of: a single shot multibox detector (SSD) architecture, you only look once (YOLO) architecture, and RetinaNet architecture.

In some embodiments, the neural network model comprises a plurality of parameters trained using a set of training data comprising: a plurality of training sets of images of H&E stained slides of tissue sections from ovaries, each training set of images from the plurality of training sets of images being from one of a plurality of different subjects, where the plurality of different subjects: (i) had been treated with a same or different compound, (ii) had not been treated with the same or different compound, or (iii) a combination thereof, and a plurality of sets of bounding boxes, each bounding box associated with the CL identified in one of the images from the plurality of training sets of images, where the loss function relates the parameters and the plurality of training sets of images to the plurality of sets of bound boxes, and the focal loss down-weights bounding boxes predicted during training for non-CL morphology or background within the plurality of training sets of images and focuses training on bounding boxes predicted for the CL.

In some embodiments, at least one training set of images of the plurality of training sets of images are adjusted before being used in training according to differences in image mean for each of a plurality of color channels of the images within the at least one training set of images, the differences in image means calculated relative to another set of training images of the plurality of training sets of images.

In some embodiments, the image mean for each of a plurality of color channels of the images is calculated as an average value of the color channel across the images within the at least one training set of images.

In some embodiments, the method further includes identifying, using the neural network model, the one or more objects within the set of images as being the CL, where the identifying comprises generating a probability score for each object of the one or more objects that is identified as the CL, and the counting comprises only counting the bounding boxes within the set of images around the one or more objects identified as the CL and having a probability score greater than a predetermined probability score threshold.

In some embodiments, the determining the ovarian toxicity comprises comparing the CL count for the ovary to a predetermined toxicity threshold, when the CL count is above the predetermined toxicity threshold, determining the compound at the amount is not toxic to the ovary, and when the CL count is below or equal to the predetermined toxicity threshold, determining the compound at the amount is toxic to the ovary.

In some embodiments, the set of images of the tissue slices are obtained from an ovary of a subject treated with the amount of the compound, and the method further includes: obtaining another set of images of tissue slices from another ovary of the subject treated with the amount of the compound; generating, using the neural network model, the another set of images with a bounding box around each object of objects that is identified as the CL within the another set of images based on coordinates predicted for the bounding box; counting the bounding boxes within the another set of images output from the deep learning neural network to obtain another CL count for the another ovary; and averaging the CL count for the ovary and the another CL count for the another ovary to obtain an averaged CL count, where the ovarian toxicity of the compound at the amount is determined based on the average CL.

In some embodiments, the method further includes: obtaining another set of images of tissue slices from one or more other ovaries that are either untreated or treated with a different amount of the compound; generating, using the neural network model, the another set of images with a bounding box around each object of objects that is identified as the CL within the another set of images based on coordinates predicted for the bounding box; and counting the bounding boxes within the another set of images output from the deep learning neural network to obtain another CL count for the ovary, where the ovarian toxicity of the compound at the amount or at the different amount is determined based on a trend between the CL count for the one or more ovaries and the another CL count for the one or more other ovaries.

In some embodiments, the method further includes: obtaining another set of images of tissue slices from one or more other ovaries that are treated with an amount of a different compound; generating, using the neural network model, the another set of images with a bounding box around each object of objects that is identified as the CL within the another set of images based on coordinates predicted for the bounding box; counting the bounding boxes within the another set of images output from the deep learning neural network to obtain another CL count for the ovary of the another subject, and determining an ovarian toxicity of the different compound at the amount based on the CL count for the one or more other ovaries.

In some embodiments, the method further includes providing the set of images with the bounding box around each object of the objects that is identified as the CL, the CL count for the one or more ovaries, the ovarian toxicity of the compound at the amount, or any combination thereof.

In some embodiments, the method further includes administering a treatment with the compound based on the ovarian toxicity of the compound at the amount.

In some embodiments, the method further includes manufacturing or having manufactured the compound based on the ovarian toxicity of the compound at the amount.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures:

FIGS. 6A, 6B, 6C, and 6D illustrate performance of an example model where errors in CL counts from the trained model were similar to inter-pathologist variations and the CL counts from the trained model was highly correlated with the pathologist's results in accordance with various embodiments;

Figure 1:
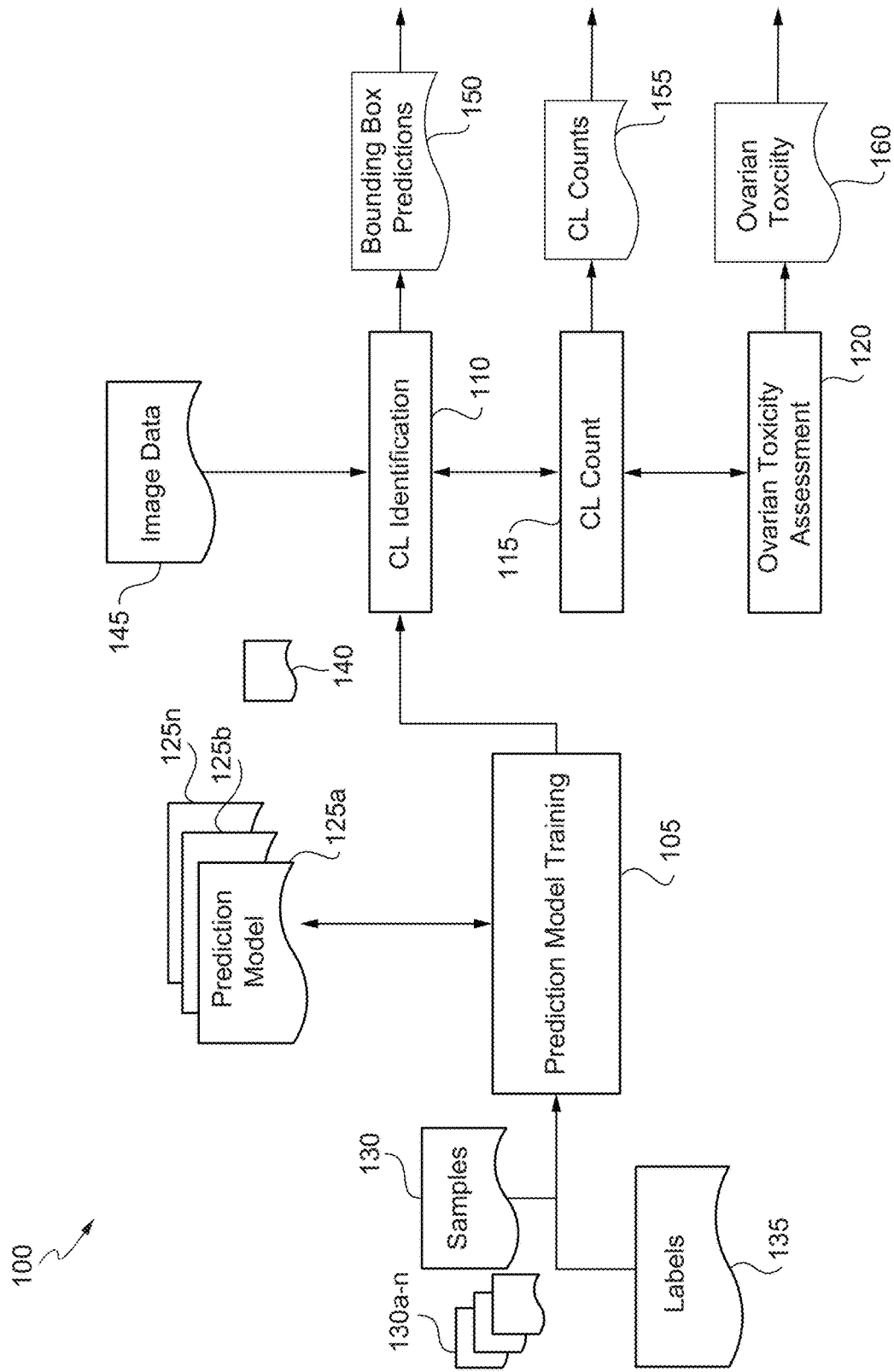
FIG. 1 shows an example computing environment for ovarian toxicity assessment in accordance with various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

The present disclosure describes techniques for assessment of ovarian toxicity. More specifically, various embodiments of the present disclosure provide a deep learning neural network that can identify CL in the ovaries and a rules-based technique that can count the CL identified in the ovaries and infer an ovarian toxicity of a compound based on the count of the CL.

The identification of ovarian pathology in animal toxicity (e.g., murine studies) studies is important in the general safety assessment of novel therapeutics. In some patient populations, the tolerability of drug-related ovarian toxicity needs to be carefully considered in terms of patient risk/benefit and specific information about ovarian pathology may inform clinical management of reproductive toxicity, such as the potential need for egg preservation and other fertility-sparing procedures.

The current gold standard for evaluation of the ovary in general toxicity and fertility studies is histopathologic examination by pathologists of hematoxylin and eosin (H&E) stained sections. A pathologist typically will assess the presence or absence of CL, the stage and number of follicles, and integrate pathologic changes in the ovary in context with the histologic changes in other organs of the reproductive tract. Given a rat's short estrus cycle of approximately 4-6 days, there is considerable dynamic structural and physiologic heterogeneity of rodent ovaries. This may make it difficult to identify clear test article-related effects (e.g., effects from therapeutic candidate compounds) using standard single section evaluation.

In a cross-industry collaborative study comparing adequacy of ovarian histopathology evaluation of a single H&E section from repeat dose and fertility studies, both significant increases and decreases in CL numbers were identified by pathologists as evidence of ovarian toxicity. (Sanbuissho, A., Yoshida, M., Hisada, S., Sagami, F., Kudo, S., Kumazawa, T., Ube, M., Komatsu, S., Ohno, Y., 2009. Collaborative work on evaluation of ovarian toxicity by repeated-dose and fertility studies in female rats. J Toxicol Sci 34 Suppl 1, SP1-22). However, the enumeration of CL from single tissue sections has been reported to suffer from sampling errors. (Meredith, S., Dudenhoeffer, G., Jackson, K., 1999. Single-section counting error when distinguishing between primordial and early primary follicles in sections of rat ovary of different thickness. J Reprod Fertil 117(2), 339-343). Moreover, Bucci et al. also demonstrated that follicle counts from the 1% sample strategy had a larger error term. (Bolon, B., Bucci, T. J., Warbritton, A. R., Chen, J. J., Mattison, D. R., Heindel, J. J., 1997. Differential follicle counts as a screen for chemically induced ovarian toxicity in mice: results from continuous breeding bioassays. Fundam Appl Toxicol 39(1), 1-10). In addition, given the large numbers of animals included in a single study compounded by the numerous ovarian structures that need to be assessed on each tissue section, a histopathologic assessment of these sections is time consuming and have the potential for errors. Although the quantification of CL from studies with a single H&E section can detect ovarian toxicity, limited studies have investigated the influence of ovary sectioning location nor tissue area on CL counts and interpretation of potential test article (e.g., therapeutic candidate compounds) due to the sectioning location and number of sections examined histologically. Given all this, stereology or a modified stereological approach to quantify CL or follicles should be performed for a thorough morphological characterization of the ovary, but this type of analysis requires time-consuming examination and manual annotations of serial sections by a pathologist.

To address these limitations and problems, the techniques described herein for assessment of ovarian toxicity include the use of a deep learning neural network that can identify corpora lutea in the ovaries and a rules-based technique that can count the CL identified in the ovaries and infer an ovarian toxicity of a compound based on the count of the CL. One illustrative embodiment of the present disclosure is directed to a method comprising: obtaining a set of images of tissue slices from one or more ovaries treated with an amount of a compound; inputting the set of images into a neural network model constructed as a one-stage detector using focal loss as at least a portion of the loss function; identifying, using the neural network model, objects within each image of the set of images; predicting, using the neural network model, coordinates for a bounding box around one or more object of the objects that are identified as CL based on the identifying of the objects; outputting, using the neural network model, the set of images with the bounding box around each object of the one or more objects that are classified as the CL based on the coordinates predicted for the bounding box; counting the bounding boxes within the set of images output from the deep learning neural network to obtain a CL count for the ovary; and determining an ovarian toxicity of the compound at the amount based on the CL count for the ovary.

Advantageously, these approaches provide a deep neural network architecture that can accurately identify CL in ovaries and reproducibly detect ovarian toxicity, which potentially reduces the workload of pathologists, including reducing the time and expense of examination and manual annotations of serial sections of ovaries. Moreover, these approaches can provide automated digital image analysis of Haematoxylin and Eosin stained (H&E stain) sections to quantify CL in ovaries (e.g., mammalian ovaries) with accuracy similar to the gold standard pathologist light microscopic assessment. By utilizing H&E stained sections, the need for special stains can be avoided (e.g., progesterone/prolactin to highlight CL) which would add cost and time delays in the routine screening of therapeutic candidate compounds.

II. Definitions

As used herein, when an action is "based on" something, this means the action is based at least in part on at least a part of the something.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As used herein, a "subject" encompasses one or more cells, tissue, or an organism. The subject may be a human or non-human, whether in vivo, ex vivo, or in vitro, male or female. A subject can be a mammal, such as a human, mouse, or rat.

As used herein, a "compound" is two or more different elements chemically bonded together. A compound may be a therapeutic candidate compound such as an antibody or pharmacological drug.

III. Techniques for Assessment of Ovarian Toxicity

In various embodiments, the assessment of ovarian toxicity is split into two parts. A first part of the assessment includes using a deep learning neural network to identify CL in the ovaries. The deep learning neural network is constructed with a modified loss function (i.e., a focal loss) to down-weight easy examples, and thus focus training on hard negatives and overcome an unbalanced nature of the training data used for training the deep learning neural network. Moreover, the deep learning neural network may be trained using an augmented data set such that a trained deep learning neural network is capable of identifying CL within the ovarian morphology over an expanded range of colors and/or color saturation levels seen in typical use case images of ovarian slices. The trained deep learning neural network takes as input images of ovarian slices and outputs images with bounding boxes around each instance of an inferred CL within the ovarian slices. In some instances, each bounding box has an associated probability score of a CL being present in the bounding box. A second part of the assessment includes using a rules-based technique to count the CL for an ovary and infer an ovarian toxicity of a compound based on the count of the CL. Thereafter, the images with the bounding boxes and probability scores for instances of CL, the count of the CL, and/or the ovarian toxicity of a compound are output for storage and use by an end user.

III.A. Example Computing Environment

FIG. 1 illustrates an example computing environment 100 (i.e., a data processing system) for ovarian toxicity assessment using deep learning neural networks according to various embodiments. As shown in FIG. 1, the ovarian toxicity assessment performed by the computing environment 100 in this example includes several stages: a model training stage 105, a CL identification stage 110, a CL count stage 115, and a ovarian toxicity assessment stage 120. The model training stage 105 builds and trains one or more models 125a-125n ('n' represents any natural number) (which may be referred to herein individually as a model 125 or collectively as the models 125) to be used by the other stages. The model 125 can be a machine-learning ("ML") model, such as a convolutional neural network ("CNN"), e.g. an inception neural network, a residual neural network ("Resnet"), a RetinaNet, a single shot multibox detector ("SSD") network, a you only look once ("YOLO") network, or a recurrent neural network ("RNN"), e.g., long short-term memory ("LSTM") models or gated recurrent units ("GRUs") models, or any combination thereof. The model 125 can also be any other suitable ML model trained in object detection from images, such as a three-dimensional CNN ("3DCNN"), a dynamic time warping ("DTW") technique, a hidden Markov model ("HMM"), etc., or combinations of one or more of such techniques—e.g., CNN-HMM or MCNN (Multi-Scale Convolutional Neural Network). The computing environment 100 may employ the same type of model or different types of models for the identification of CL in ovaries. In certain instances, model 125 is constructed with focal loss as a loss function, which compensates for the imbalanced nature within each image between the non-CL morphology of the ovaries and the CL in the ovaries, as described in further detail herein.

To train a model 125 in this example, samples 130 are generated by acquiring digital images, splitting the images into a subset of images 130a for training (e.g., 90%) and a subset of images 130b for validation (e.g., 10%), preprocessing the subset of images 130a and the subset of images 130b, augmenting the subset of images 130a, and annotating the subset of images 130a with labels 135. The images are of ovarian tissue sections and may be acquired from a data storage structure such as a database, an image system (e.g., a light microscope camera), or the like (e.g., 5× magnification scans of ovarian tissue sections may be extracted from 20× scans obtained by the camera of a light microscope). The images may be of ovarian tissue sections from various levels within the right and/or left ovaries of one or more subjects. In some instances, the images are of ovarian tissue sections stained with a histology stain such as Carmine, Silver nitrate, Giemsa, Trichrome Stains, Gram Stain, Haematoxylin, and H&E stain. In certain instances, the histology stain is H&E stain. In certain instances, the images within the subset of images 130a for training are acquired in accordance with a protocol or constraint such that substantial all or all of the images are of the ovaries of subjects that had not been treated with a compound and have normal counts of CL (e.g., 1 to 1.5 counts/tissue area $mm^2$). Whereas, the images within the subset of images 130b for validation are acquired in accordance with a different protocol or constraint such that some of the images are of the ovaries of subjects that had not been treated with a compound and have normal counts of CL (e.g., 1.0 to 1.5 counts/tissue area mm²), some of the images are of the ovaries of subjects that had been treated with a compound and are abnormal with a drop off in count of CL (e.g., 0.5 to 1.0 counts/tissue area mm²), and/or some of the images are of the ovaries of subjects that had been treated with a compound and are abnormal with a very low count of CL (e.g., 0.0 to 0.5 counts/tissue area mm²).

The splitting may be performed randomly (e.g., a 90/10% or 70/30%) or the splitting may be performed in accordance with a more complex validation technique such as K-Fold Cross-Validation, Leave-one-out Cross-Validation, Leave-one-group-out Cross-Validation, Nested Cross-Validation, or the like to minimize sampling bias and overfitting. The preprocessing may comprise cropping the images such that each image only contains a single ovary section. In some instances, the preprocessing may further comprise standardization or normalization to put all features on a same scale (e.g., a same size scale or a same color scale or color saturation scale, as described herein in further detail). In certain instances, the images are resized with a minimum side (width or height) of predetermined pixels (e.g., 2500 pixels) or with a maximum side (width or height) of predetermined pixels (e.g., 3000 pixels) and kept with the original aspect ratio.

Augmentation can be used to artificially expand the size of the subset of images 130a by creating modified versions of images in the datasets. Image data augmentation may be performed by creating transformed versions of images in the datasets that belong to the same class as the original image. Transforms include a range of operations from the field of image manipulation, such as shifts, flips, zooms, and the like. In some instances, the operations include random erasing, shifting, brightness, rotation, Gaussian blurring, and/or elastic transformation to ensure that the model 125 is able to perform under circumstances outside those available from the subset of images 130a. Augmentation can additionally or alternatively be used to artificially expand the color spectrum and/or color saturation level for images that the model 125 can take as input after deployment, as described herein in further detail. Color spectrum and/or color saturation level augmentation may be performed by obtaining the differences in image mean for color and/or color saturation (e.g., the red channel) between the images of a group of images of the subset of images 130a (e.g., images acquired from a first toxicology study) and the image means for color and/or color saturation (e.g., the red channel) of one or more other groups of images of the subset of images 130a (e.g., images acquired from other toxicology studies), multiplying the differences with random factors (e.g., a range from −20 to −40) to obtain an expanded color spectrum and/or color saturation level, and adding the expanded color spectrum and/or color saturation level to a different group of images of the subset of images 130a for additional data augmentation. This additional data augmentation can improve performance of the model 125 for images input for inference from various sources or studies.

Annotation can be performed manually by one or more humans (annotators such as a pathologist(s)) confirming the presence of one or more instances of CL in each image of the subset of images 130a and providing labels 135 to the one or more instances of CL, for example, drawing a bounding box (a ground truth), using annotation software, around the area confirmed by the human to include one or more instances of CL. In certain instances, the bounding box may only be drawn for instances that have a greater than 50% in probability of being a CL. For the images, which are annotated by multiple annotators, the bounding boxes from all annotators are used. When the same CL was identified by multiple annotators, individual annotations are combined into a single bounding box. The smaller bounding boxes are replaced with the larger bounding boxes. The total CL counts for each image may be computed by counting the number of bounding boxes in each ovary section and the information may be annotated to the images using the labels 135.

The training process for model 125 includes selecting hyperparameters for the model 125 and performing iterative operations of inputting images from the subset of images 130a into the model 125 to find a set of model parameters (e.g., weights and/or biases) that minimizes a loss or error function for the model 125. The hyperparameters are settings that can be tuned or optimized to control the behavior of the model 125. Most models explicitly define hyperparameters that control different aspects of the models such as memory or cost of execution. However, additional hyperparameters may be defined to adapt a model to a specific scenario. For example, the hyperparameters may include the number of hidden units of a model, the learning rate of a model, or the convolution kernel width for a model. Each iteration of training can involve finding a set of model parameters for the model 125 (configured with a defined set of hyperparameters) so that the value of the loss or error function using the set of model parameters is smaller than the value of the loss or error function using a different set of model parameters in a previous iteration. The loss or error function can be constructed to measure the difference between the outputs inferred using the models 125 (in this example, the bounding boxes around one or more instances of CL) and the ground truth bounding boxes annotated to the images using the labels 135.

Once the set of model parameters are identified, the model 125 has been trained and can be validated using the subset of images 130a (testing or validation data set). The validation process includes iterative operations of inputting images from the subset of images 130b into the model 125 using a validation technique such as K-Fold Cross-Validation, Leave-one-out Cross-Validation, Leave-one-group-out Cross-Validation, Nested Cross-Validation, or the like to tune the hyperparameters and ultimately find the optimal set of hyperparameters. Once the optimal set of hyperparameters are obtained, a reserved test set of images from the subset of images 130b are input into the model 125 to obtain output (in this example, the bounding boxes around one or more instances of CL), and the output is evaluated versus ground truth bounding boxes using correlation techniques such as Bland-Altman method and the Spearman's rank correlation coefficients and calculating performance metrics such as the error, accuracy, precision, recall, receiver operating characteristic curve (ROC), etc.

As should be understood, other training/validation mechanisms are contemplated and may be implemented within the computing environment 100. For example, the model may be trained and hyperparameters may be tuned on images from the subset of images 130a and the images from the subset of images 130b may only be used for testing and evaluating performance of the model. Moreover, although the training mechanisms described herein focus on training a new model 125. These training mechanisms can also be utilized to fine tune existing models 125 trained from other datasets. For example, in some instances, a model 125 might have been pre-trained using images of other biological structures (non-ovarian sections) or from ovarian sections from other subjects or studies (e.g., human trials or murine experiments). In those cases, the models 125 can be used for transfer learning and retrained/validated using the samples 130 as discussed herein.

The model training stage 105 outputs trained models including one or more trained CL object detection models 140. The one or more CL object detection models 140 may be used in the CL identification stage 110 to obtain bounding boxes around each instance of an inferred CL with an associated probability score of a CL being present in the bounding box. The CL identification stage 110 may include processes (e.g., instructions which, when executed on one or more data processors, cause the one or more data processors to perform part or all of one or more methods and/or part or all of one or more processes) for obtaining image data 145. In some instances, the obtaining includes acquiring images of ovarian tissue sections from a data storage structure such as a database, an image system, or the like. The images may be of ovarian tissue sections from various levels within the right and/or left ovaries of one or more subjects. In some instances, the images are of ovarian tissue sections stained with a histology stain such as Carmine, Silver nitrate, Giemsa, Trichrome Stains, Gram Stain, Haematoxylin, and H&E stain. The images within the image data 145 may be of the ovaries of the same or different subjects untreated or treated with the same or different compound.

The CL identification stage 110 may further include optional processes for preprocessing image data 145. In some instances, the preprocessing comprises standardization or normalization to put all features on a same scale (e.g., a same size scale or a same color scale or color saturation scale, as described herein in further detail). In certain instances, the images are resized with a minimum side (width or height) of predetermined pixels (e.g., 2500 pixels) or with a maximum side (width or height) of predetermined pixels (e.g., 3000 pixels) and kept with the original aspect ratio. The CL identification stage 110 further includes processes for inputting the image data 145 (with or without preprocessing) into the CL object detection models 140 and executing the CL object detection models 140. The CL object detection models 140 infer one or more instances of CL within each image based on the model parameters, and output images 150 with bounding boxes around each instance of an inferred CL. In certain instances, each bounding box has an associated probability score of a CL being present in the bounding box.

The CL count stage 115 includes processes (e.g., instructions which, when executed on one or more data processors, cause the one or more data processors to perform part or all of one or more methods and/or part or all of one or more processes) for obtaining or receiving the output images 150 from the CL identification stage 110. The CL count stage 115 further includes processes for executing a rules-based technique to count the inferred one or more instances of CL in the output images 150. In some instances, the rules-based technique may count the bounding boxes in each image associated with an ovary from a subject to obtain a total count 155 of CL for the ovary. In other instances, the rules-based technique may count the bounding boxes in each image associated with a first ovary (e.g., left ovary) from a subject to obtain a total count 155 of CL for the first ovary, and count the bounding boxes in each image associated with a second ovary (e.g., right ovary) from a subject to obtain a total count 155 of CL for the second ovary. In certain instances, the rules-based technique may take the average (or apply another like statistical approach) of the total count of CL for the first ovary and the total count of CL for the second ovary to obtain an average CL count 155 for the subject. Bounding boxes with a probability score of less than predetermined threshold (e.g., 0.5 or 0.75) may not be counted by the rules-based technique. In yet other instances, the rules-based technique may use any other counting method for the bounding boxes in each image associated with a sample, which optionally takes into consideration the associated probability score, to obtain a total count of CL for the sample.

The CL ovarian toxicity assessment stage 120 includes processes (e.g., instructions which, when executed on one or more data processors, cause the one or more data processors to perform part or all of one or more methods and/or part or all of one or more processes) for obtaining or receiving the total or average count 155 from the CL count stage 115. The CL ovarian toxicity assessment stage 120 further includes processes for executing a rules-based technique to infer an ovarian toxicity 160 (a mammalian ovarian toxicity) of a compound based on the total or average count 155. The ovarian toxicity may be determined across different amounts and different compounds using the same CL object detection models 140. Firstly, it was surprising discovered how well and accurately the individual count of the CL tracks with ovarian toxicity of a compound (as supported by the data discussed herein with respect to the examples). Conventionally an ovarian toxicity assessment for a compound or environment is based on qualitative and quantitative analysis of a number of factors including follicle morphology and count in combination with CL presence/absence. Secondly, it was surprising discovered how well and accurately the individual count of the CL tracks with ovarian toxicity assessment for a wide array of different compounds (as supported by the data discussed herein with respect to the examples for multiple compounds).

In some instances, the rules-based technique may infer ovarian toxicity 160 as a binary result (e.g., yes the compound is toxic or no the compound is not toxic) from the total or average count 155 based on a predetermined toxicity threshold (e.g., a total or average CL count below 1.5 counts/tissue area $mm^2$ is indicative of toxicity of the compound for the ovary). In other instances, the rules-based technique may infer ovarian toxicity 160 as a binary result (e.g., yes the compound is toxic or no the compound is not toxic) from a trend of the total or average count 155 associated with two or more dosage levels of a compound (e.g., a baseline or no compound introduced to the subject and dosage level of the compound introduced to the subject). In yet other instances, the rules-based technique may use any other inference method (e.g., non-binary) for the toxicity assessment associated with a sample, which optionally takes into consideration two or more dosage levels of a compound, to determine an ovarian toxicity 160 of a compound.

While not explicitly shown, it will be appreciated that the computing environment 100 may further include a developer device associated with a developer. Communications from a developer device to components of the computing environment 100 may indicate what types of input images are to be used for the deep learning neural network, a number and type of deep learning neural networks to be used, hyperparameters of each deep learning neural network, for example, learning rate and number of hidden layers, how data requests are to be formatted, which training data is to be used (e.g., and how to gain access to the training data) and which validation technique is to be used, and/or how the rules-based techniques are to be configured.

III.B. Exemplary Data Augmentation for Model Training

In some embodiments, the deep learning neural network is trained on images of ovarian sections from the ovaries of subjects that had not been treated with a compound and have been stained with a histology stain such as Carmine, Silver nitrate, Giemsa, Trichrome Stains, Gram Stain, Haematoxylin, and H&E stain. The histology stain is a colorant used to visualize native morphology within a sample, and is not a stain such as a immunohistochemistry stain for selectively identifying specific structures within the sample. This allows for the deep learning neural network to be trained and used on images obtained through an inexpensive and fairly simple staining processes such as H&E stain as compared to images obtain through a more expensive and complex staining process such as immunohistochemistry stains.

However, samples stained with histology stain have a tendency for variation in color (e.g., H&E stain can result in the same structure of a sample being stained along a color spectrum between dark purple to light pink). This variation in color can be due to variation in the stain or staining process, for example, variation in timing of the staining processes, e.g., leaving a stain on a slide for a long period time versus a short period of time may result in darker or lighter colors, and variation in constituents used to make the stain, e.g., different chemicals in the water used to reconstitute pigments or dyes may result in different colors along a spectrum. In order to address this variation in color and/or saturation level, the images of the training data are augmented such that the deep learning neural network is trained to identify CL within the ovarian morphology over an expanded range of colors and/or color saturation levels. Further, traditional techniques such as color mapping of the RGB color of the images from other data sets would be insufficient for addressing this variation problem because such changes normally introduce noise (in either hue, saturation, or value) of the remapped color, which would affected model performance. Instead, to address these limitations and problems, an augmentation technique is provided to capture differences in colors and/or color saturation between different subsets of training data, augment one or more subsets of training data with the captured differences to obtain an augmented subset of training data, and train the deep learning neural network using the original subsets of training data and the augmented subset of training data to expand the color space and color saturation levels that the deep learning neural network can take as input after deployment.

More specifically, the augmentation may be performed by obtaining the differences in image mean for color and/or color saturation (e.g., the red channel) between the images of a group of images from training data (e.g., images acquired from a first toxicology study) and the image means for color and/or color saturation (e.g., the red channel) of one or more other groups of images from the training data (e.g., images acquired from other toxicology studies). The calculated differences are then multiplied with random factors (e.g., a range of random values from −20 to −40, 0 to −40, −10 to −60, etc.) to obtain an expanded color spectrum and/or color saturation level. The expanded color spectrum and/or color saturation is added (augmented images=original images+difference*random factor) to generate one or more groups of images of the training data for data augmentation.

As an example, assume hypothetical study A has 2 images (image-1 and image-2) to be used as training data, and hypothetical study B has 2 images (image-3 and image-4) to be used as training data. In study A, the image-1-red (image-1-R) channel (total across each image) and the image-2-R channel are averaged to a single number meanAR, and similarly for the green and blue channels to generate numbers meanAG and meanAB. In study B, the image-1-R channel and the image-2-R channel are averaged to a single number meanBR, and similarly for the green and blue channels meanBG and mean BB.

The difference in image mean (for each color) may then be computed as follows:

Difference in red $dR = meanAR - meanBR$

Difference in green $dG = meanAG - meanBG$

Difference in blue $dB = meanAR - meanBB$

The difference in red, green, and blue (dR, dB, and dG) are multiplied with random factors (e.g., a range of random values from −20 to −40, 0 to −40, −10 to −60, etc.) to obtain an expanded color spectrum and/or color saturation level (exR, exB, and exG). The expanded color spectrum and/or color saturation level (exR, exB, and exG) are added to the RGB channels for the 2 images of study A and/or the 2 images of Study B to obtain a set of augmented images. The original 2 images from each of Study A and Study B and the augmented images are then used to train the model. This data augmentation can improve performance of the model for images input for inference from various sources or studies (images that tend to have variation in color and and/or color saturation).

III.C. Exemplary Deep Learning Neural Network

In various embodiments, a deep learning neural network is provided that can identify CL in the ovaries (an object detection task that comprises predicting all four coordinate values which describe a bounding box). For an object detection task, two different approaches can be used: (i) make a fixed number of predictions on grid (one stage), (ii) or leverage a proposal network to find objects and then use a second network to fine-tune the proposals and output a final prediction (two stage). One stage detection (i.e., directly) was chosen for the deep learning network of the present embodiments because it is easier to train on a smaller set of available training data and it is a much simpler and faster model architecture. In some instances, the deep learning neural network is a CNN, e.g. an inception neural network, a Resnet, a RetinaNet, or any combination thereof.

The deep learning neural network is trained on images of ovarian sections from the ovaries of subjects at various stages of the estrous cycle and have not been treated with a compound (e.g., therapeutic candidate compound). This ensures a large enough pool of images for training that will have on average a CL count of about 10 to 30 CLs per ovary and about 1 to 1.5 CL counts/tissue area $mm^2$ for each slice. However, the images will have a large amount of non-CL ovarian morphology and background as compared to the small amount of CL, if any, and thus have a large set of candidate locations for bounding boxes are dominated by easily classified background examples. The creates a class imbalance problem for one stage detectors because during training the model often ends up with a large amount of bounding boxes in which no object is contained due to the nature of our "predictions on a grid" approach without an intermediate step of regional proposal to narrow down the number of candidate object locations to a smaller number. Conventionally, this class imbalance problem is addressed via bootstrapping or online hard example mining. But those techniques would not work efficiently in this instance because: (i) the training samples being used all contain CL (the positive class) and thus a sequence of images without CL could not be used for bootstrapping purposes, and (ii) online hard example mining completely discards easy examples, which would be a major portion of the training data set causing another class imbalance problem.

In order to overcome the class imbalance problem and achieve an accurate identification and quantification of CL with a limited training data set, the deep learning neural network is constructed with a modified loss function (i.e., a focal loss). The focal loss compensates for the imbalanced nature of the images by reshaping cross entropy loss such that it down-weights the loss assigned to well-classified examples and focuses training on hard negatives. For example, cross entropy loss for a binary classification is expressed as:

$$CE(p, y) = \begin{cases} -\log(p) & \text{if } y = 1 \\ -\log(1 - p) & \text{otherwise.} \end{cases}$$

where $y \in \{\pm 1\}$ is the ground-truth class and $p \in [0,1]$ is the model's estimated probability. For notation convenience, $p_t$ is defined and CE is rewritten as:

$$p_t = \begin{cases} p & \text{if } y = 1 \\ 1 - p & \text{otherwise,} \end{cases}$$

$$CE(p, y) = CE(p_t) = -\log(p_t)$$

This cross entropy loss function CE is reshaped by adding a modulating factor $(1-p_t)^\gamma$ to the cross entropy loss CE where $\gamma$ is a prefixed positive scala value or a focusing parameter.

$$FL(p_t) = -(1-p_t)^\gamma \log(p_t)$$

Accordingly, when an example is misclassified and $p_t$ is small, the modulating factor $(1-p_t)^\gamma$ is near 1 and the loss is unaffected. As $p_t \to 1$, the modulating factor $(1-p_t)^\gamma$ goes to 0 and the loss for well-classified examples is down-weighted. The focusing parameter $\gamma$ smoothly adjusts the rate at which easy examples are down-weighted. When $\gamma=0$, FL is equivalent to CE. When $\gamma$ is increased, the effect of the modulating factor $(1-p_t)^\gamma$ is likewise increased. The focal loss is essentially a means to avoid the gradient being overtaken by the accumulation of the losses of easy examples (e.g., all the non-CL ovarian morphology and background). Instead, the focal loss focuses training on the sparse set of hard examples (e.g., rare instances of CL) and prevents the vast number of easy negatives (e.g., the non-CL ovarian morphology and background) from overwhelming the detector during training.

Figure 2:
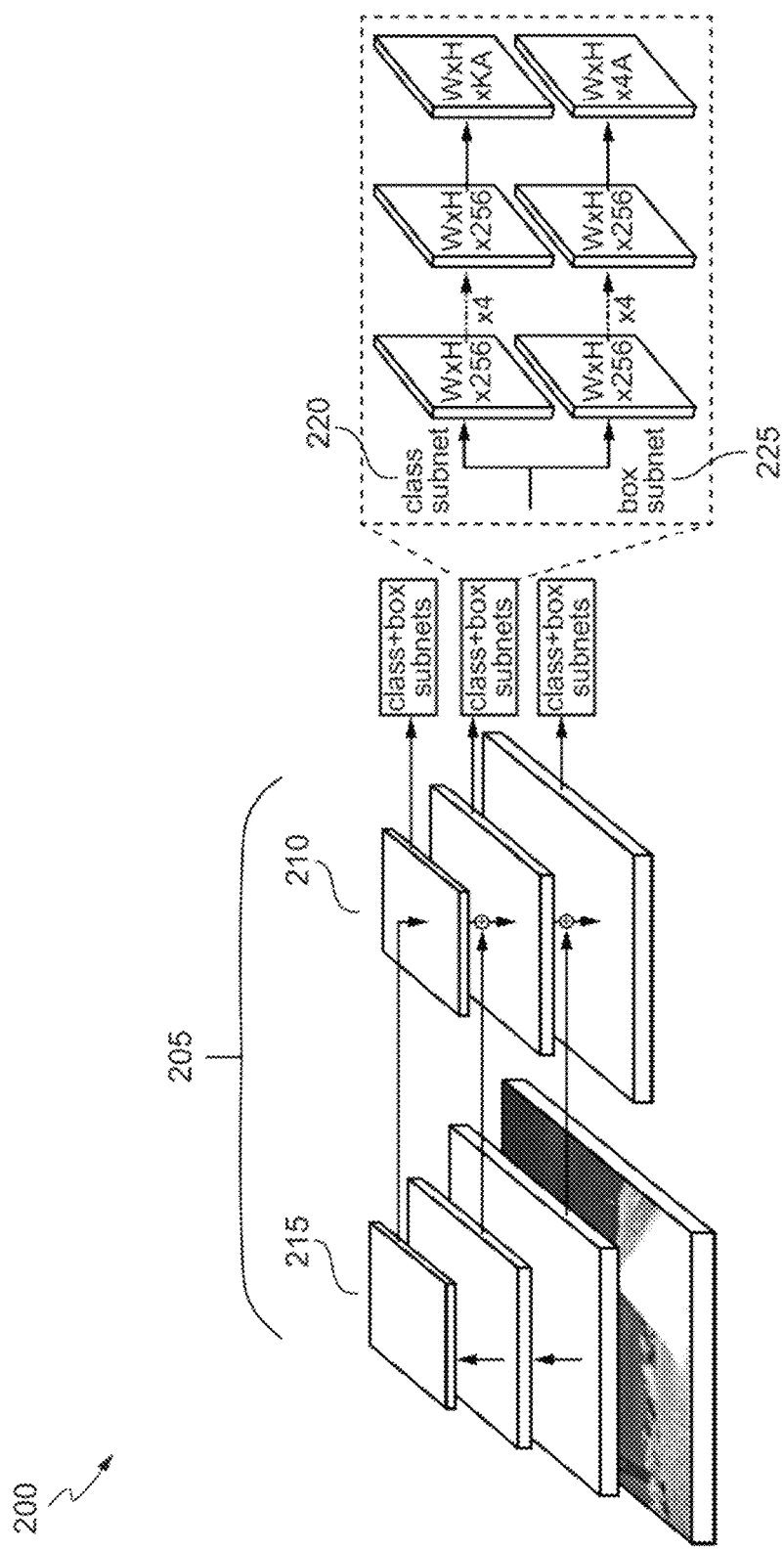
FIG. 2 shows an exemplary schematic diagram representative of a RetinaNet architecture in accordance with various embodiments.

In various embodiments, the focal loss is implemented in a RetinaNet as the classification loss function. As shown in FIG. 2, the RetinaNet 200 may be comprised of: (i) a backbone network 205 comprised of a feature pyramid network 210 built on top of a ResNet 215 in a fully convolutional manner, which allows the backbone network 205 to take an image of an arbitrary size and output proportionally sized feature maps at multiple levels in the feature pyramid network 210, (ii) a first subnetwork 220 responsible for predicting the probability of an object being present at each spatial location for each anchor box and object class using the backbone's output, and (iii) a second subnetwork 225 responsible for regressing the offset for the bounding boxes from the anchor boxes for each ground-truth object using the backbone's output. The ResNet 215 provides a bottom-up pathway, which calculates the feature maps at different scales, irrespective of the input image size or the backbone. Some consecutive layers of the ResNet 215 may output feature maps of the same scale, but generally, feature maps of deeper layers have smaller scales/resolutions. The bottom-up pathway is accomplished by choosing the last feature map of each group of consecutive layers that output feature maps of the same scale.

These chosen feature maps are used as the foundation of the feature pyramid network 210, which provides a top-down pathway and lateral connections. The top down pathway upsamples the spatially coarser feature maps from higher pyramid levels, and the lateral connections merge the top-down layers and the bottom-up layers with the same spatial size. More specifically, using nearest neighbor upsampling, the last feature map from the bottom-up pathway is expanded to the same scale as the second-to-last feature map. These two feature maps are then merged by element-wise addition to form a new feature map. This process is iterated until each feature map from the bottom-up pathway has a corresponding new feature map connected with lateral connections. The higher level feature maps contain grid cells that cover larger regions of the image and are therefore more suitable for detecting larger objects; in contrast, grid cells from lower level feature maps are better at detecting smaller objects. These feature maps can be used independently to make predictions for bounding boxes, and thus contribute to a model that is scale-invariant and can provide better performance both in terms of speed and accuracy.

The first subnetwork 220 is a fully convolutional network (FCN) attached to each level of the feature pyramid network 210 and predicts the probability of an object being present at each spatial location for each anchor box (A) and object class (K). The first subnetwork 220 may be comprised of multiple (e.g., four) convolutional layers with multiple filters (e.g., 256), followed by rectified linear unit (RELU) activations. Subsequently, another convolutional layer with K×AK×A filters may be applied, followed by sigmoid activation. The first subnetwork 220 has shared parameters across all levels. The shape of the output feature map may be (W,H,KA), where W and H are proportional to the width and height of the input feature map, K and A are the numbers of object class and anchor box. Each anchor box is responsible for detecting the existence of objects from K classes in the area that it covers. Therefore, each anchor box corresponds to K numbers indicating the class probabilities, and because there are A bounding boxes per grid, the output feature map of first subnetwork 220 has KA channels.

The second subnetwork 225 is a regression subnet that is attached to each feature map of the feature pyramid network 210 and is in parallel to the first subnetwork 220. The design of the second subnetwork 225 is identical to that of the first subnetwork 220, except that the last convolutional layer has 4A filters. Therefore, the shape of the output feature map would be (W,H,4A) where W and H are proportional to the width and height of the input feature map, A is the numbers of anchor box. Both the first subnetwork 220 and the second subnetwork 225 have output feature maps with width W and height H, where each of the W×H slices corresponds to a region in the input image. In addition to the first subnetwork 220 detecting the existence/class of objects, each anchor box is also responsible for detecting the size/shape of objects. This is done through the second subnetwork 225, which outputs 4 numbers for each anchor box that predict the relative offset (in terms of center coordinates, width and height) between the anchor box and the ground truth box. Therefore, the output feature map of the regression subnet has 4A channels. Accordingly, the subnets generate multiple values (K from the first subnetwork 220, 4A channels from the second subnetwork 225) for a total number expressed as:

$$\Sigma_{l=3}^{7} W_l \times H_l$$

where l denotes the level of pyramid, and W and H are the width and height of the output feature map of the subnet of anchor boxes. Using these numbers to refine the anchor boxes, it is possible for the model to output predictions for the 4 coordinates of the bounding boxes.

To calculate the loss for training the RetinaNet 200, a comparison is made between the predictions for the 4 coordinates of the bounding boxes and the coordinates of the bounding boxes for the ground truths. The loss of RetinaNet is a multi-task loss that contains two terms: one for localization (denoted as $L_{loc}$) and the other for classification (denoted as $L_{cls}$). The multi-task loss can be expressed as:

$$L = \lambda L_{loc} + L_{cls}$$

where λ is a hyperparameter that controls the balance between the two task losses $L_{loc}$ and $L_{cls}$. The localization loss ($L_{loc}$) and the classification loss (Las) are calculated based on the comparison made between the predictions for the 4 coordinates of the bounding boxes and the coordinates of the bounding boxes for the ground truths. The localization loss ($L_{loc}$) is a regression loss. As discussed herein, for each anchor box with a match, the second subnet 225 predicts four numbers. The first two numbers specify the offset between the centers of the anchor box and ground truth while the last two numbers specify the offset between the width/height of the anchor box and the ground truth. Correspondingly, for each of these predictions, there is a regression target computed as the offset between the anchor box and the ground truth. The regression loss can be defined based on this regression target. The classification loss ($L_{cls}$) is a focal loss, as discussed in detail herein. The focal loss reduces the loss contribution from easy examples and increases the importance of correcting misclassified examples.

RetinaNet 200 generates predictions for four coordinate values which describe a bounding box around inferred instances of CL in the ovaries. For each input image of an ovarian section, there are a number of anchor boxes from all levels of the feature pyramid network 210 expressed as:

$$\Sigma_{l=3}^{7} W_l \times H_l \times A$$

For each anchor box, the first subnetwork 220 predicts K numbers indicating the probability distribution of the presence of CL in the image, while the second subnetwork 225 predicts four numbers indicating the offset between each anchor box and the corresponding bounding box. For performance considerations, a hyperparameter of the RetinaNet 200 can be set such that the model selects at most a predetermined number of anchor boxes (e.g., 100) that have the highest probability score of a CL being present in the bounding box from each level of the feature pyramid network 210, or selects anchor boxes (e.g., 100) that exceed a predetermined threshold probability score (e.g., 0.75) of a CL being present in the anchor box from each level of the feature pyramid network 210, or a combination thereof based on a predetermined number of anchor boxes and a predetermined threshold probability score. Only these anchor boxes will be included in the remaining stages performed by the RetinaNet 200. At this stage, a CL in the image may be predicted with multiple anchor boxes. To remove redundancy, non-maximum-suppression (NMS) may be applied to the CL prediction, which iteratively chooses an anchor box with the highest probability score and removes any overlapping anchor boxes with an Intersection over Union greater than a set value such as 0.5. In the last stage, for each remaining anchor box for a CL identification, the second subnetwork 225 gives offset predictions that may be used to refine the anchor box to get a final bounding box prediction for each instance of identified CL.

IV. Techniques for Ovarian Toxicity Assessment

Figure 3:
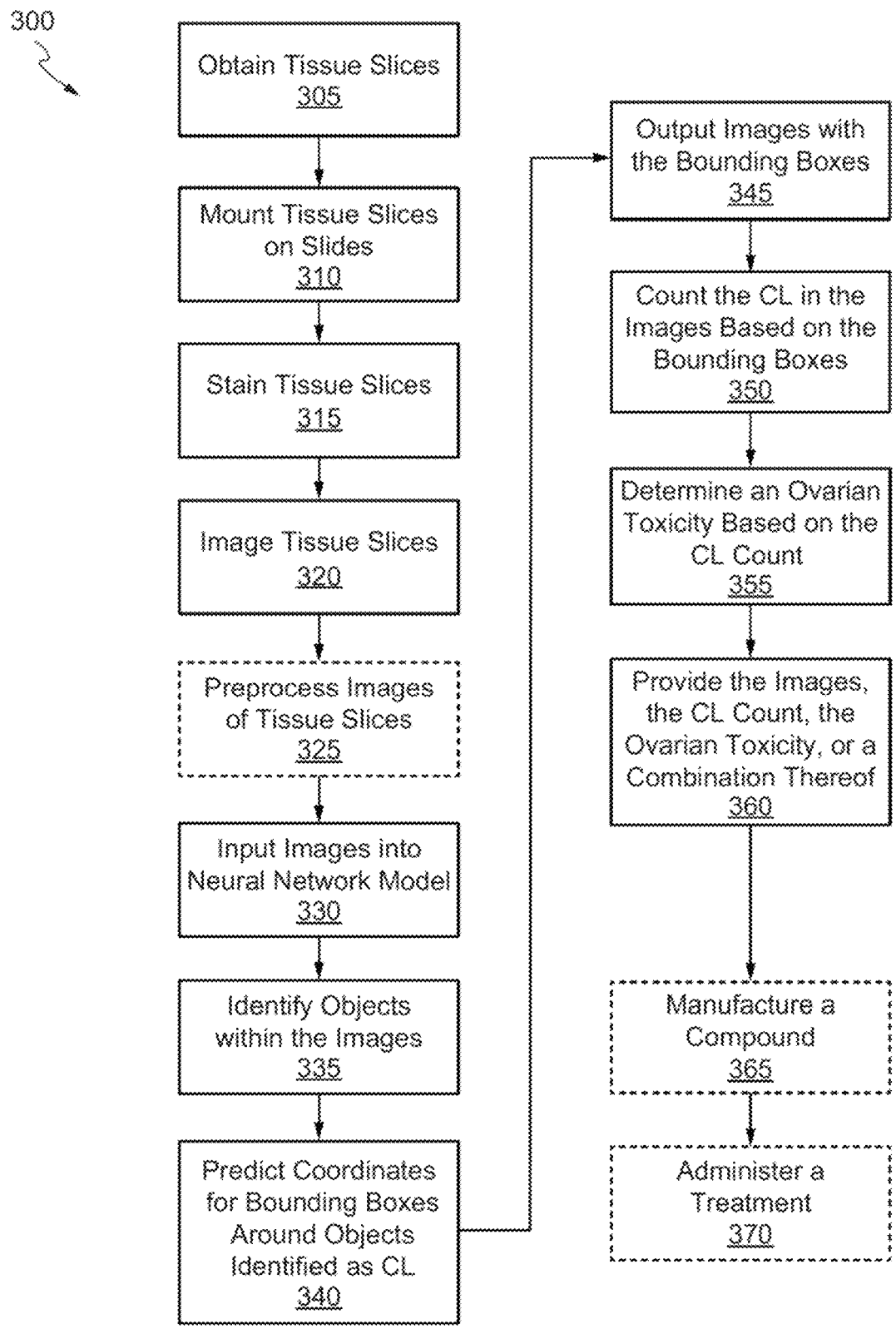
FIG. 3 shows a process for assessing ovarian toxicity in accordance with various embodiments.

FIG. 3 shows a process 300 for an ovarian toxicity assessment in accordance with various embodiments.

Process 300 begins at block 305, at which tissue slices are obtained from one or multiple ovaries of one or multiple subjects (e.g., the left and right ovaries of a murine subject). In some instances, the subject(s) have been treat with an amount of a compound (e.g., a dose of a therapeutic). In other instances, the subject(s) have not been treated with an amount of compound (e.g., a baseline). At block 310, the tissue slices are mounted onto slides. The slides being a substrate for use with microscopy. At block 315, the slides are treated with a histology stain such as H&E stain. In certain instances, the plurality of slides are not treated with any other stains other than the H&E stain. At block 320, each slide is imaged with an imaging device (e.g., a camera mounted to a microscope) to generate images for the tissue slices. The images may be a set of images that comprise at least one image of a tissue slice from each ovary of the multiple ovaries. The association between image and ovary may be maintained in the image data using an identifier such as a metadata tag or the like.

At optional block 325, the images for the tissue slices are preprocessed. The preprocessing may comprise cropping the images such that each image only contains a single ovary section. In some instances, the preprocessing may further comprise standardization or normalization to put all features on a same scale (e.g., a same size scale or a same color scale or color saturation scale, as described herein in further detail). In certain instances, the images are resized with a minimum side (width or height) of predetermined pixels (e.g., 2500 pixels) or with a maximum side (width or height) of predetermined pixels (e.g., 3000 pixels) and kept with the original aspect ratio.

At block 330, the images are input into a neural network model constructed as a one-stage detector using focal loss as at least a portion of the loss function. The inputting may comprise inputting iteratively each image from a set of images of the tissue slices from one ovary, then inputting iteratively each image from another set of images of the tissue slices from another ovary, and repeating this process until all sets of images within the images have been processed by the neural network model.

The neural network model may be structured based on an object detection model architecture such as a SSD architecture, YOLO architecture, or a RetinaNet architecture. In some instances, the neural network model comprises a plurality of parameters trained using a set of training data comprising: (i) a plurality of training sets of images of stained slides such as H&E stained slides of tissue sections from ovaries, each training set of images from the plurality of training sets of images being from one of a plurality of different subjects, and (ii) a plurality of sets of bounding boxes, each bounding box associated with the CL identified in one of the images from the plurality of training sets of images. The loss function of the neural network model relates the parameters and the plurality of training sets of images to the plurality of sets of bound boxes, and the focal loss down-weights bounding boxes predicted during training for non-CL morphology or background within the plurality of training sets of images and focuses training on bounding boxes predicted for the CL. In certain instances, at least one training set of images of the plurality of training sets of images are adjusted before being used in training according to differences in image mean for each of a plurality of color channels of the images within the at least one training set of images, the differences in image means calculated relative to another set of training images of the plurality of training sets of images. The image mean for each of a plurality of color channels of the images is calculated as an average value of the color channel across the images within the at least one training set of images.

At block 335, one or more objects within the images are identified as being CL using the neural network model (e.g., the identification could be performed as part of a classification schema of CL objects from background objects or as a multi-class classification schema of CL objects from other ovarian structures and/or cell types and background objects). In some instances, the CL is identified or classified based on features maps generated via a feature pyramid network within the neural network model. In certain instances, the identifying or classifying comprises generating a probability score for each object of the one or more objects that are identified or classified as the CL. At block 340, coordinates are predicted for a bounding box around one or more objects of the objects that are identified as CL based on the identifying or classifying of the objects from block 335. At block, 345, the images with the bounding box around one or more objects of the objects that are identified as the CL are output based on the coordinates predicted for the bounding box.

At block 350, the bounding boxes within the images output from the deep learning neural network are counted to obtain a CL count for the one or multiple ovaries of the one or multiple subjects. A CL count can be generated based on a per subject count where all bounding boxes within the images associated with a given subject (one or multiple ovaries of the subject) are counted to obtain the CL count. Alternatively, a CL count can be generated based on a per ovary count where all bounding boxes within images associated with a given ovary are counted to obtain the CL count. Thereafter, the CL account generated for each ovary associated with a same subject may be averaged to obtain an averaged CL count for the subject. In certain instances, the counting comprises only counting the bounding boxes within the images around the objects classified as the CL and having a probability score greater than a predetermined probability score threshold. In other instances, At block 355, an ovarian toxicity is determined for the compound at the amount (e.g., the dose of a therapeutic) based on the CL count for the ovary or subject, or the average CL count for the subject. The ovarian toxicity may be determined across different amounts and different compounds using the same neural network model. In some instances (e.g., when the images are obtained from a subject exposed to a single amount of a compound), the determining the ovarian toxicity comprises comparing the CL count for the ovary or subject, or the average CL count for the subject to a predetermined toxicity threshold. When the CL count for the ovary or subject, or the average CL count for the subject is above the predetermined toxicity threshold, the compound at the amount is determined not toxic to the ovary. When the CL count for the ovary or subject, or the average CL count for the subject is below or equal to the predetermined toxicity threshold, the compound at the amount is determined toxic to the ovary. In other instances (e.g., when the images are obtained from multiple subjects exposed to multiple amounts of a compound (images from subjects that have been treated with multiple amounts of compounds and baseline images from subjects that have not been treated with any amount of a compound)), the determining the ovarian toxicity comprises comparing a first CL count for the ovary or subject, or the average CL count for the subject to a second, third, fourth, etc. CL count for another ovary or subject, or the average CL count for another subject, and determining a trend between the first, second, third, fourth, etc. CL counts based on the comparison, and determining the ovarian toxicity based on the trend. For example, if the trend shows the CL count going down with increased amounts of compound then it may be determined that the compound is toxic to the ovary. Whereas, if the trend shows the CL count stable with increased amounts of compound then it may be determined that the compound is not toxic to the ovary. This determination based on the trend may further take into consideration the predetermined toxicity threshold to better understand and infer at which amount the compound is toxic or not toxic to the ovary.

At block 360, the set of images with the bounding box around each object of the objects that is classified as the CL, the CL count for the ovary, the ovarian toxicity of the compound at the amount, or any combination thereof are provided. For example, the set of images, the CL count for the ovary, the ovarian toxicity of the compound at the amount, or any combination thereof may be locally presented or transmitted to another device. The set of images, the CL count for the ovary, the ovarian toxicity of the compound at the amount, or any combination thereof may be output along with an identifier of the subject. In some instances, the set of images, the CL count for the ovary, the ovarian toxicity of the compound at the amount, or any combination thereof is output to an end user or storage device. At optional block 365, the compound is manufactured or have been manufactured based on the ovarian toxicity of the compound at the amount. At optional block 370, a treatment is administered with the compound based on the ovarian toxicity of the compound at the amount.

V. Examples

The systems and methods implemented in various embodiments may be better understood by referring to the following examples.

V.A. Example 1.—Ovarian Sections from Jive Repeat Dose Toxicity Studies

Ovarian sections from five repeat dose toxicity studies conducted in support of completed compound development programs were included in this retrospective study. Female Sprague-Dawley rats were used for all five studies.

V.A.1 Study Design and Training Overview

Figure 4:
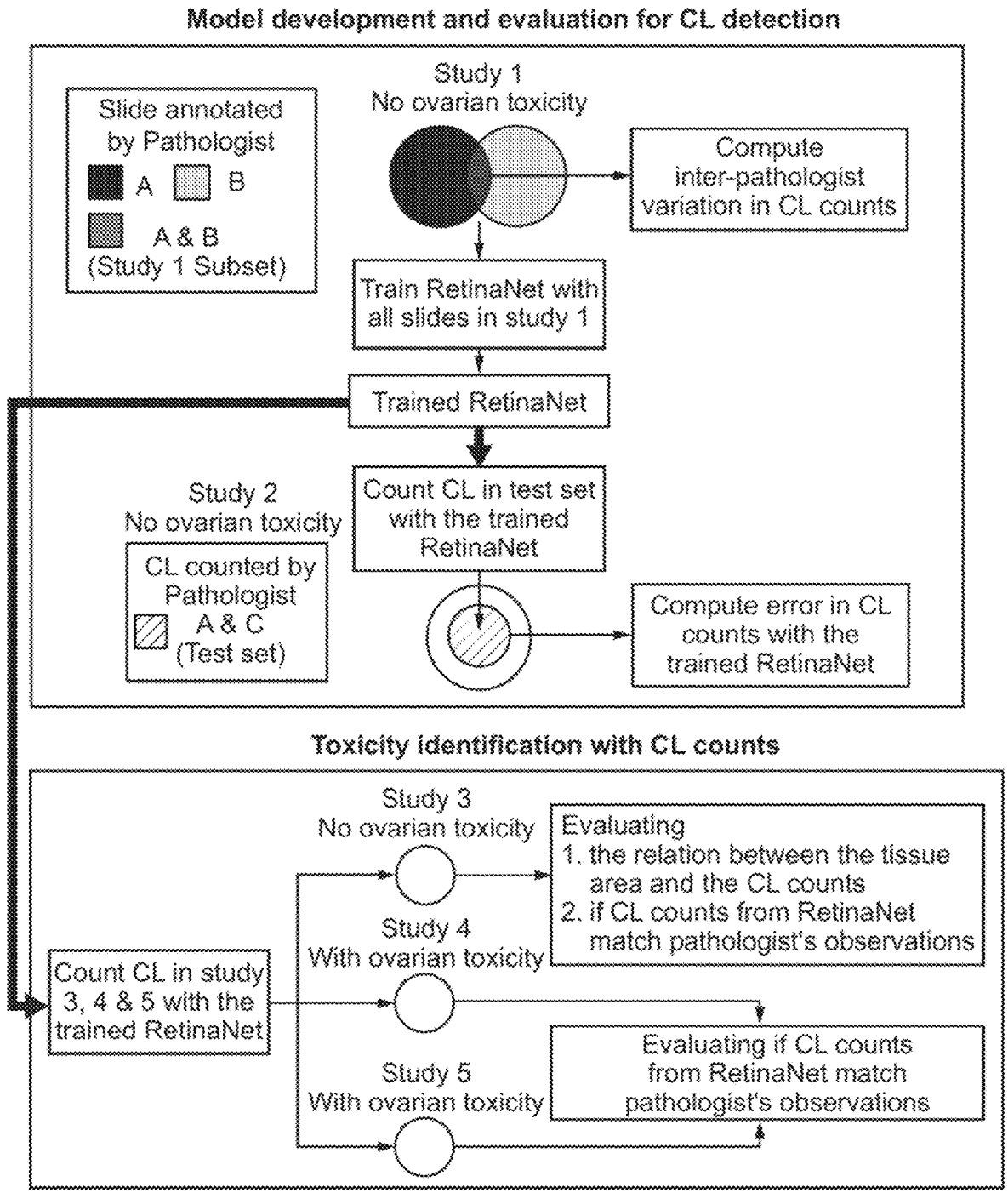
FIG. 4 shows a flow chart illustrating an example method and example model for detecting ovarian toxicity in accordance with various embodiments.
Figures 5A, 5B, 5C, 5D:
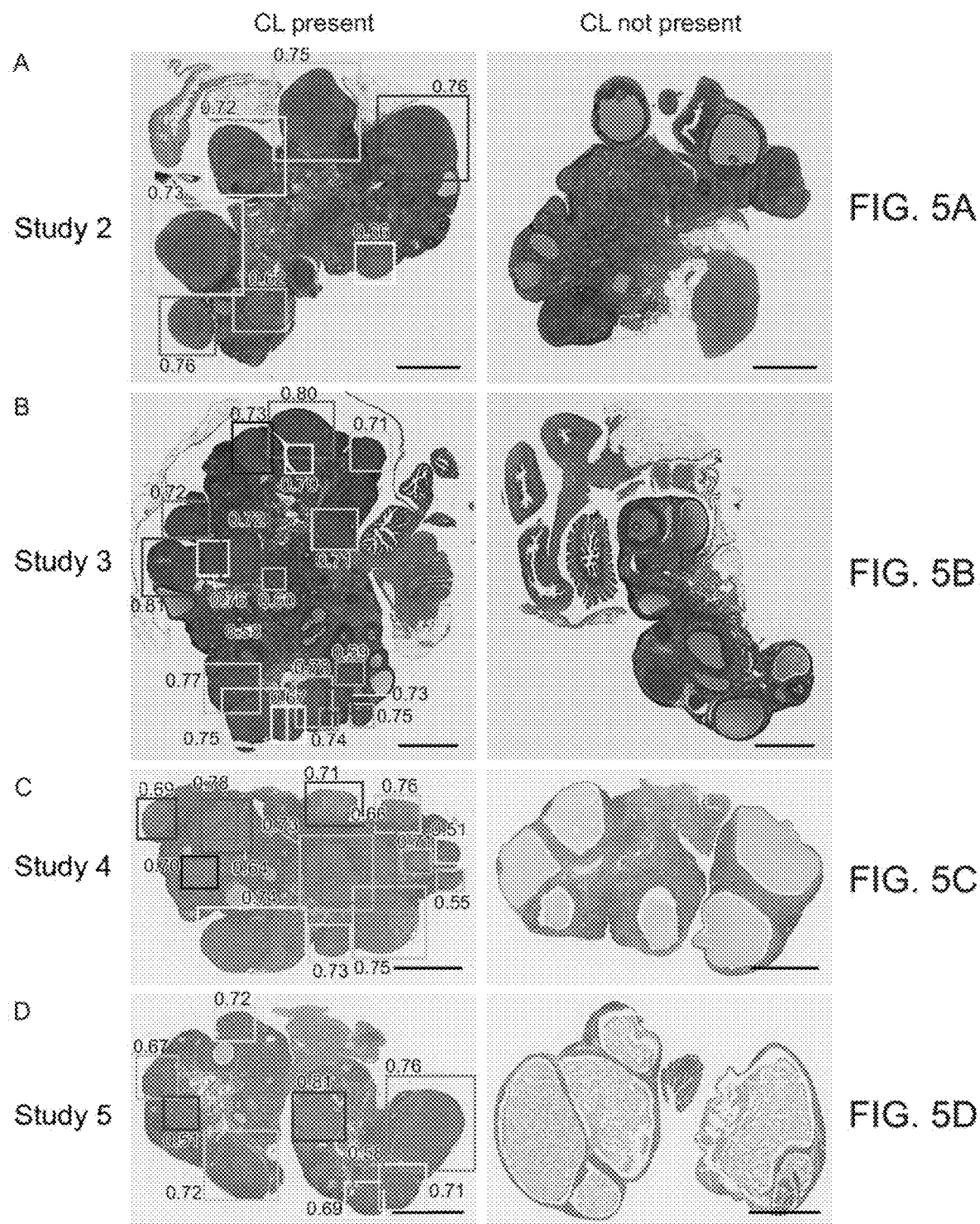
FIGS. 5A, 5B, 5C, and 5D illustrate that a trained example model can accurately detect CL in accordance with various embodiments.

FIG. 4 summarizes the study design for this example. An object detection deep learning neural network, in an example embodiment discussed herein a RetinaNet, was trained with all sections from Study 1 (90% of sections for the training set and 10% of sections for the validation set) to identify CL. The model was trained with the annotations from Pathologists A and B on the training set. A subset of sections in Study 1 (Study 1 Subset) was also annotated by both Pathologist A and Pathologist B and served as part of the validation set. Within this subset, Pathologists A and B were blinded to each other's annotations and the variations were computed. Next, in a subset of sections in Study 2, CL were counted by Pathologists A and C and used as the gold standard test set. The trained model was applied to this same test set to evaluate the accuracy of the model in CL counting compared to the gold standard. The accuracy of the CL counts from the model in the test set was compared to the inter-pathologist variation in Study 1. In the final step of validation, the model was applied to studies with and without ovarian pathology findings to investigate if the deep learning method results in observations similar to those from pathologists. The model CL counts between treated and control groups were compared for Studies 3, 4 and 5. The relation between the tissue area and CL counts were also investigated in Study 3. Table 1 summarizes the five toxicity studies and whether or not ovarian pathology was observed by the pathologists for each study.

Table 1 illustrates a summary of the study designs. Study 1 was annotated by two pathologists and was used for training and validating the model. Study 2 was used for evaluating the agreement between the model and the pathologists. CL counts for Studies 3, 4, 5 were obtained from the model. *50 rats underwent 15 weeks of recovery period after the 26 weeks of dosing. **Only 79 of the 100 animals had manual CL count from the pathologists.

V.A.3 Manual Annotation from Pathologists

All H&E sections in Study 1 were manually annotated by Pathologist A and Pathologist B for CL. Bounding boxes were drawn around all CL present in the tissue section for identification purposes using Aperio ImageScope. The total CL counts were computed by counting the number of bounding boxes in each ovary section. To evaluate the inter-pathologist variation, 224 ovary H&E sections from all levels were randomly selected and annotated by both pathologists. These 224 sections were defined as Study 1 Subset as described previously. The remaining ovary sections were split in half and annotated by either Pathologist A or Pathologist B. For Study 2, only the total CL counts from the test set (155 ovary sections) were reported from Pathologist A and C. The total CL counts were not reported for the remaining ovary sections in Study 2. No CL were manually annotated by pathologists for Studies 3, 4 and 5.

V.A.4 Image Processing, Model Training and Inference

Images at 5× magnification were extracted from the 20× scans for all studies. Ovarian tissue was identified using Otsu's method after the images were converted to grayscale.

| Study | Compound | Dose per group (mg/kg/day) | Study duration (week) | Total serial sections per ovary | Total number of female animal | Total number of female animal used | Total number of ovary section used | Treatment effect in ovary observed by pathologist | Has manual CL counts from pathologists | Used for training or testing |
|---|---|---|---|---|---|---|---|---|---|---|
| 1 | A | 0,15,50,100 | 26 | 6 | 80 | 80 | 956 | No | Yes | Training: CL detection |
| 2 | B | 0,100 | 26,41* | 1 | 100 | 79** | 155 | No | Yes | Testing: CL detection |
| 3 | A | 0,10,50,150,500 | 13 | 6 | 75 | 75 | 900 | No | No | Testing: Tox detection |
| 4 | C | 0,50,100,200 | 13 | 1 | 40 | 40 | 80 | Yes | No | Tox detection |
| 5 | D | 0,10,30,100 | 4 | 1 | 40 | 40 | 80 | Yes | No | Testing: Tox detection |

V.A.2 Histology Sections and Digitization

In the studies, rats were examined macroscopically at necropsy and fixed for processing to sections for microscopic examination. Though it was anticipated that a single H&E section would be adequate for our analyses, it was investigated whether or not step sections of the ovary would potentially change the general conclusion of the individual study outcome (changes in CL number as compared to control), therefore six 5 μm thick sections 150 μm apart were prospectively analyzed. Sections were labeled as L1 (as defined by the first step section), L2, L3, L4, L5 and L6 (the last step section, and likely has the least amount of tissue in the block), respectively. Individual 150 μm step sections were chosen based on the size of CL to detect most individual CL while limiting the likelihood of capturing the same CL in multiple sections. Based on findings from analyzing the step sections, the studies proceeded with using a single 5 μm thick H&E section from each ovary for Studies 2, 4 and 5. All H&E sections were digitized using whole slide bright field scanners. Sections from Studies 1, 2 and 3 were scanned with a Nanozoomer scanner and sections from Studies 4 and 5 were scanned with an Aperio scanner at 20× magnification.

Next, the images were cropped so that each image only contained a single ovary. The area of the ovary was computed by summing the number of positive pixels after Otsu's threshold value was applied.

In one example embodiment, a RetinaNet comprised of a deep residual neural network (50-layer version) as a backbone was used for CL detection. A pre-trained deep residual neural network from ImageNet was used for transfer learning. The cropped ovary images and the annotations from Study 1 were used to train the RetinaNet. For the Study 1 Subset, which were both annotated by Pathologist A and Pathologist B, the bounding boxes from both pathologists were used. When the same CL was identified by both pathologists, individual annotations were combined into a single bounding box. The smaller bounding boxes were replaced with the larger bounding boxes.

The sections in Study 1 were randomly split into training (90%) and validation sets (10%). The cropped images were resized with a minimum side (width or height) of 2500 pixels or with a maximum side (width or height) of 3000 pixels and kept with the original aspect ratio. Random erasing, shifting, brightness, rotation, Gaussian blurring and elastic transformation were used for data augmentation to ensure that the model was able to perform under circumstances outside those available from the training data alone.

Particularly, the various studies were captured under different scenarios, such that without more the model may have been performant on images captured in a manner similar to Study 1, but not necessarily other studies (e.g., Studies 4 and 5).

Further, traditional augmentation techniques such as color mapping of the RGB color of the other study images would have been insufficient. Such changes normally introduce noise (in either hue, saturation, or value) of the remapped color, which would have affected model performance. To address this issue, the differences in image mean between the images of Study 1 and the image means of the images of the other studies were multiplied with random factors (range from −20 to −40) and added to the original training images for additional data augmentation. This additional data augmentation improved model performance for images inserted for inference from the various studies.

Model training was performed with a step size of 3000 for 30 epochs using a batch size of 1. The Smooth L1 loss ($\sigma=3$) was used for regression loss and the Focal loss ($\alpha=0.4$ and $\gamma=2$) was used for classification loss. Adam optimizer was used (learning rate=1×10-5) for optimization.

The trained model was applied to the cropped ovary images in Study 2, 3, 4 and 5. During the inference, the cropped ovary images were first resized using the same methods as described above and then fed to the trained model. Bounding boxes with probability scores of CL were generated after the application of the trained model to the cropped ovary images. Bounding boxes with less than 0.5 in probability scores were ignored. The total numbers of model identified CL were counted for each ovary. The average CL counts from both left and right ovaries were also computed.

V.A.5 Statistical Analysis

In order to evaluate the accuracy of the example model discussed in the previous section in total CL counts, the trained model was tested in a study with a different experimental protocol and was validated against a co-evaluation from the pathologists' A and C in the test set. The Bland-Altman method and the Spearman's rank correlation coefficients were used to assess the agreement in total CL count per ovary between Pathologist A and Pathologist B in the Study 1 Subset as well as the agreement between the co-evaluation from Pathologists (A and C) and the trained model in the test set.

It was expected that the tissue area is linearly correlated with the CL count. To evaluate the relationship between the tissue area and CL count in association with the sectioning level, Spearman's rank correlation coefficients were computed between the tissue area and the CL count from all levels as well as at each level in Study 3. Since tissues with a smaller area are likely to have fewer CL, the CL count was divided by the ovary tissue area for normalization. The Kruskal-Wallis tests were performed among the normalized CL count from all levels as well as among the normalized CL counts from all treated and control groups in Study 3. Next, the average CL count normalized to tissue area from all levels were computed per rat. The average CL count normalized to tissue area between the treated groups (low, mid and high dose) and the control group in Study 3, 4 and 5 were compared using Wilcoxon rank sum test respectively. Image analyses and statistical analyses were performed with Python. The model was trained using Keras/Tensorflow. The training and inferring were performed using a single graphics processing unit (Nvidia, P6000).

V.A.6 Detail Study Protocols for Each Toxicity Study

Study 1: A total of 80 rats were included in Study 1. The rats were split into control, low, mid and high dose groups with 20 rats per group and Compound A was administered twice daily via oral gavage with a dose level of 0, 15, 50 and 100 (mg/kg/day) in vehicle (0.5% (w/v) hydroxypropyl methylcellulose and 0.2% (w/v) polysorbate 80 in reverse osmosis water, pH 3.0) for 26 weeks respectively.

Study 2: A total of female 100 rats were included in Study 2. The rats were split into 2 terminal and 2 recovery groups (n=25 rats/group). The 2 terminal groups were treated with 0 and 100 (mg/kg/day) of vehicle and Compound B in vehicle (0.5% (w/v) hydroxypropyl methylcellulose and 0.2% (w/v) polysorbate 80 in reverse osmosis water) through oral gavage twice daily respectively. The treated terminal group was mated with untreated rats 5 days following the last dose administration. After completion of the cohabitation period, the treated and untreated female rats were euthanized for pathology examination on day 13 of presumed gestation. The same dosing protocol was applied to the 2 recovery groups and the treated rats in the recovery group were mated to untreated male rats after 15 weeks of recovery following the last dose administration. After the cohabitation period, the females were euthanized on day 13 of presumed gestation.

Study 3: Seventy five rats were included in Study 3. The rats were split into control, low, mid, mid-high and high dose groups (n=15 rats/group). Compound A was administered twice daily via oral gavage with a dose level of 0, 10, 15, 150 and 500 (mg/kg/day) for 13 weeks respectively.

Study 4: Forty rats were assigned to 4 groups (n=10 rats/group; control, low, mid and high dose groups). Animals received oral doses of either vehicle (10% Polyethyleneglycol 400 (PEG)/100 mM N-methyl glucamine (NMG), pH 8.5) or Compound C in vehicle at dose levels of 50, 100, or 200 mg Compound C per kg body weight (mg/kg), once daily for 13 weeks.

Study 5: Forty rats were assigned to 4 groups (n=10 rats/group; control, low, mid and high dose groups). Animals received oral doses of either vehicle (0.5% (w/v) methylcellulose (20 to 30 cps) and 0.2% (w/v) polysorbate 80 in water for injection, pH 6.7±0.3) or Compound D in vehicle at dose levels of 10, 30, or 100 mg Compound D per kg body weight (mg/kg), once daily for 4 weeks.

V.A.6 Overall Tissue Area Analyzed Impacts the Number of CL Present

An initial step in developing and testing the method was to train the model to accurately identify CL in tissues. FIGS. 5A, 5B, 5C, and 5D show the representative images that contained multiple or no CL from Studies 2, 3 4, and 5. CL were accurately identified when present in ovarian tissues and vice versa. The number above the bounding box shows the probability score of a CL present in the box. (Scale bars: 1 mm). The presence of CL was confirmed by the pathologists in the representative images. Bounding boxes were drawn in the area that had greater than 50% in probability of containing a CL. Next, to quantify the accuracy of the trained model in CL counting, the trained model was applied to Study 2 and the result was compared to the inter-pathologist variation in Study 1 Subset. FIG. 6A shows the Bland-Altman plot assessing the inter-pathologist variation (between Pathologist A and Pathologist B) of the CL counts from 224 ovarian tissues in Study 1. FIG. 6B Bland-Altman plot assessing the agreement between the pathologist (reviewed by both Pathologist A and C) and the trained model in CL counts in Study 3 for 155 ovarian tissues. Study 2 is blinded to the model in the training process. The mean absolute difference in CL count was 0.64±0.088 (mean and standard error) between Pathologist A and Pathologist B for Study 1 Subset and the mean absolute difference in CL count was 0.57±0.096 between the pathologists and the trained model for the test set. FIG. 6C and FIG. 6D show the scatter plots for the CL counts from Pathologist A and Pathologist B in Study 1 Subset and from the pathologists and the trained model in the test set respectively. The dashed red lines indicate 95% limits of agreement. The solid red lines indicate the mean difference for the CL counts of the pathologist A vs. pathologist B or pathologists (A and C) vs. the model. The dot size represents the number of same CL count in log scale. The black dashed lines show the perfect agreement in CL counts. The CL counts were divided by the maximum CL count from Pathologist A and B for Study 1 Subset and by the maximum CL count from the pathologists and model for the test set respectively for visualization purposes. The CL counts between the Pathologist A and B were strongly correlated (R=0.99, p<<0.01) and the CL counts between the pathologists and the trained RetinaNet were strongly correlated as well (R=0.97 p<<0.01).

V.A.7 Overall Tissue Area Analyzed Impacts the Number of CL Present

Figure 7A:
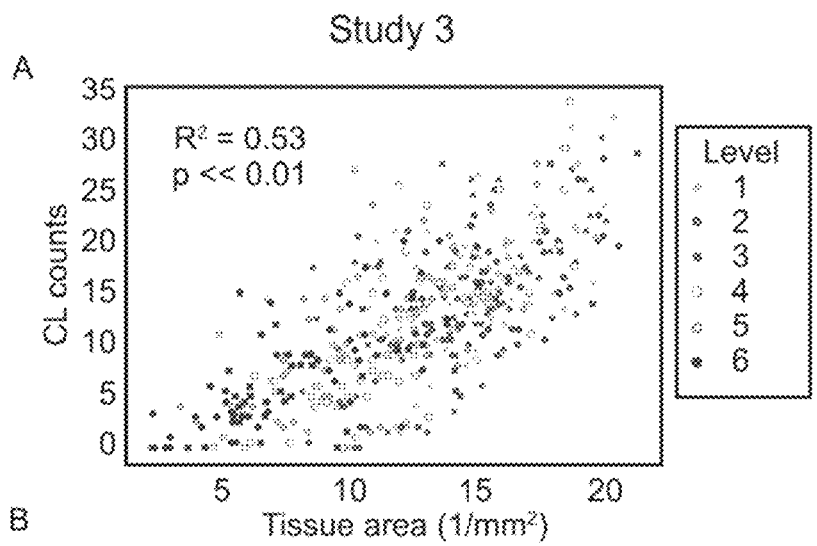
FIGS. 7A, 7B, and 7C illustrate example results indicating that CL count is impacted by ovarian tissue area and level in accordance with various embodiments.

To address questions as to whether or not additional sectioning of the ovary would impact the numbers of CL enumerated and overall interpretation of the study findings (as compared to the standard single slide), six step sections, 150 μm apart, were used for evaluation. FIG. 7A shows the scatter plot for ovary tissue area versus CL count from all levels in Study 3. When using all CL counts at all levels, a strong correlation (R=0.73, p<<0.01) between the CL count and the ovary tissue area was observed indicating that with less tissue area evaluated, there are a smaller number of CL present. At each level, the CL count and the ovary tissue area was significantly correlated as well (R=0.57, 0.52, 0.64, 0.73, 0.75, 0.73 for L1, L2, L3, L4, L5 and L6 respectively and all p<<0.01). Since the CL count was significantly correlated with the tissue area at each level, normalizing the CL count by the tissue area could mitigate the effect of tissue area. The mean and standard error of the CL count and the tissue area as well as the normalized CL count at each level were summarized in Table 2.

Table 2 illustrates a summary of the CL count and the tissue area at each level in study 3. The mean and the standard error of the CL count, the tissue area and the normalized CL count were computed. The CL count and tissue area were decreased by approximately 50% when the sectioning level changed from level 1 to 6 whereas the normalized CL count remained relatively the same. (N=75 ovary sections)

| | Level 1 | Level 2 | Level 3 | Level 4 | Level 5 | Level 6 |
|---|---|---|---|---|---|---|
| CL count | 15.14 ± 0.771 | 14.73 ± 0.731 | 13.87 ± 0.774 | 12.27 ± 0.800 | 10.26 ± 0.792 | 7.07 ± 0.596 |
| Tissue Area (mm$^2$) | 14.79 ± 0.294 | 14.87 ± 0.325 | 14.17 ± 0.363 | 12.28 ± 0.388 | 10.30 ± 0.410 | 7.78 ± 0.362 |
| CL count normalized to tissue area (1/mm$^2$) | 1.01 ± 0.046 | 0.98 ± 0.046 | 0.96 ± 0.048 | 0.96 ± 0.050 | 0.94 ± 0.060 | 0.85 ± 0.059 |

Figure 7B:
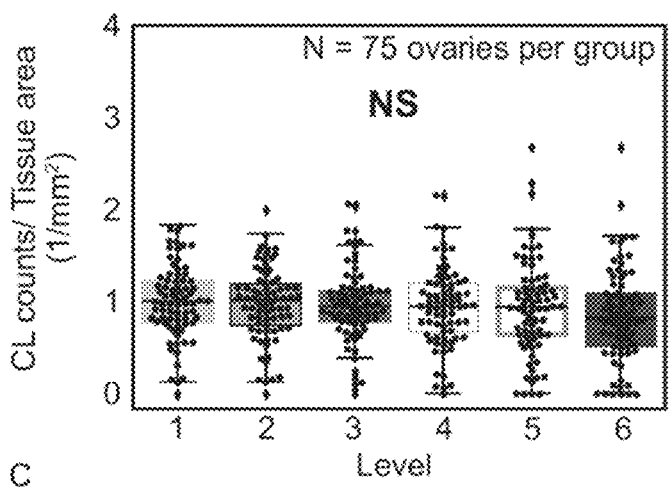

Both CL count and the tissue area decreased when the level increased. The normalized CL counts were relatively stable when the level increased. FIG. 7B shows the CL count normalized to tissue area at different levels of sectioning. No significant differences in the normalized CL count to the tissue area among all levels were observed from the Kruskal-Wallis test. To investigate the relation of the CL count and the tissue area in each level and each dose group in the Study 3, the mean and standard error of the CL count and the tissue area as well as the normalized CL count at each level for all dose groups were summarized in Table 3.

Table 3 is a summary of the CL endpoints at each level for each dose group in Study 3. The mean and the standard error of the CL count endpoints computed. Both CL count and the tissue area decreased with an increase of the level but the normalized CL count remain relatively the same for every dose group. In addition, within the same sectioning level, the CL count and the tissue area were relatively the same when no toxicity presented in the ovary for all dose groups. Since keeping the same sectioning level might be challenging, normalization is recommended. (N=15 ovary sections per level per dose group)

| Dose (mg/kg/day) | All level | Level 1 | Level 2 | Level 3 | Level 4 | Level 5 | Level 6 |
|---|---|---|---|---|---|---|---|
| | | | | Tissue area (mm$^2$) | | | |
| 0 (control) | 11.69 ± 0.929 | 14.63 ± 2.402 | 14.10 ± 2.295 | 13.20 ± 2.300 | 12.27 ± 2.456 | 9.46 ± 2.158 | 6.49 ± 1.542 |
| 10 | 13.41 ± 0.652 | 15.77 ± 1.582 | 15.30 ± 1.597 | 14.77 ± 1.528 | 13.90 ± 1.552 | 12.03 ± 1.515 | 8.70 ± 1.265 |
| 50 | 10.87 ± 0.643 | 15.43 ± 1.548 | 14.60 ± 1.257 | 12.40 ± 1.466 | 10.27 ± 1.128 | 7.63 ± 1.179 | 4.90 ± 1.003 |
| 150 | 12.50 ± 0.707 | 13.70 ± 1.309 | 14.30 ± 1.513 | 14.50 ± 1.739 | 12.53 ± 1.747 | 12.10 ± 2.125 | 7.87 ± 1.521 |
| 500 | 12.63 ± 0.727 | 16.17 ± 1.745 | 15.33 ± 1.533 | 14.47 ± 1.660 | 12.37 ± 1.918 | 10.06 ± 1.652 | 7.40 ± 1.227 |
| | | | | Tissue area (mm$^2$) | | | |
| 0 (control) | 12.54 ± 0.492 | 14.96 ± 0.941 | 15.06 ± 1.005 | 14.26 ± 1.064 | 12.60 ± 1.069 | 10.26 ± 1.163 | 8.11 ± 0.925 |
| 10 | 12.97 ± 0.413 | 14.95 ± 0.746 | 15.20 ± 0.774 | 14.64 ± 0.869 | 13.24 ± 0.869 | 11.31 ± 0.857 | 8.50 ± 0.797 |
| 50 | 11.43 ± 0.397 | 14.62 ± 0.454 | 14.31 ± 0.513 | 13.14 ± 0.622 | 10.98 ± 0.706 | 8.80 ± 0.746 | 6.76 ± 0.712 |

-continued

| Dose (mg/kg/day) | All level | Level 1 | Level 2 | Level 3 | Level 4 | Level 5 | Level 6 |
|---|---|---|---|---|---|---|---|
| 150 | 12.16 ± 0.398 | 14.37 ± 0.578 | 14.60 ± 0.714 | 13.90 ± 0.774 | 11.90 ± 0.805 | 10.53 ± 0.798 | 7.65 ± 0.821 |
| 500 | 12.72 ± 0.416 | 15.03 ± 0.532 | 15.20 ± 0.603 | 14.91 ± 0.685 | 12.69 ± 0.850 | 10.60 ± 0.960 | 7.89 ± 0.823 |
| CL count normalized to tissue area (1/mm$^2$) | | | | | | | |
| 0 (control) | 0.86 ± 0.054 | 0.90 ± 0.121 | 0.90 ± 0.121 | 0.87 ± 0.126 | 0.89 ± 0.134 | 0.84 ± 0.148 | 0.77 ± 0.147 |
| 10 | 1.06 ± 0.055 | 1.07 ± 0.112 | 1.07 ± 0.112 | 1.04 ± 0.123 | 1.08 ± 0.135 | 1.10 ± 0.154 | 1.04 ± 0.171 |
| 50 | 0.89 ± 0.039 | 1.05 ± 0.106 | 1.05 ± 0.106 | 0.92 ± 0.108 | 0.90 ± 0.078 | 0.80 ± 0.086 | 0.64 ± 0.086 |
| 150 | 0.98 ± 0.049 | 0.94 ± 0.079 | 0.94 ± 0.079 | 1.02 ± 0.104 | 1.00 ± 0.123 | 1.05 ± 0.172 | 0.88 ± 0.131 |
| 500 | 0.96 ± 0.036 | 1.06 ± 0.094 | 1.06 ± 0.094 | 0.95 ± 0.075 | 0.94 ± 0.090 | 0.91 ± 0.093 | 0.91 ± 0.104 |

Figure 7C:
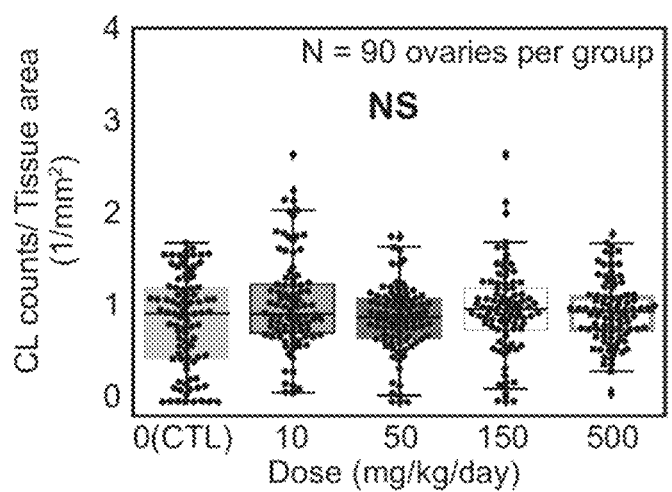

Both CL count and the tissue area decreased for each dose group when the level increased. Although the CL count and the tissue area among all dose groups were in similar range within each level, normalization can still reduce the impact of tissue area to the CL count and thus recommended. From FIG. 7C, the CL count normalized to tissue area shows that the CL counts normalized to tissue area for all dose groups were not significantly different. The CL count normalized to the tissue area were relatively stable across different levels and dose groups compared to the raw CL count.

Figures 8A, 8B, 8C:
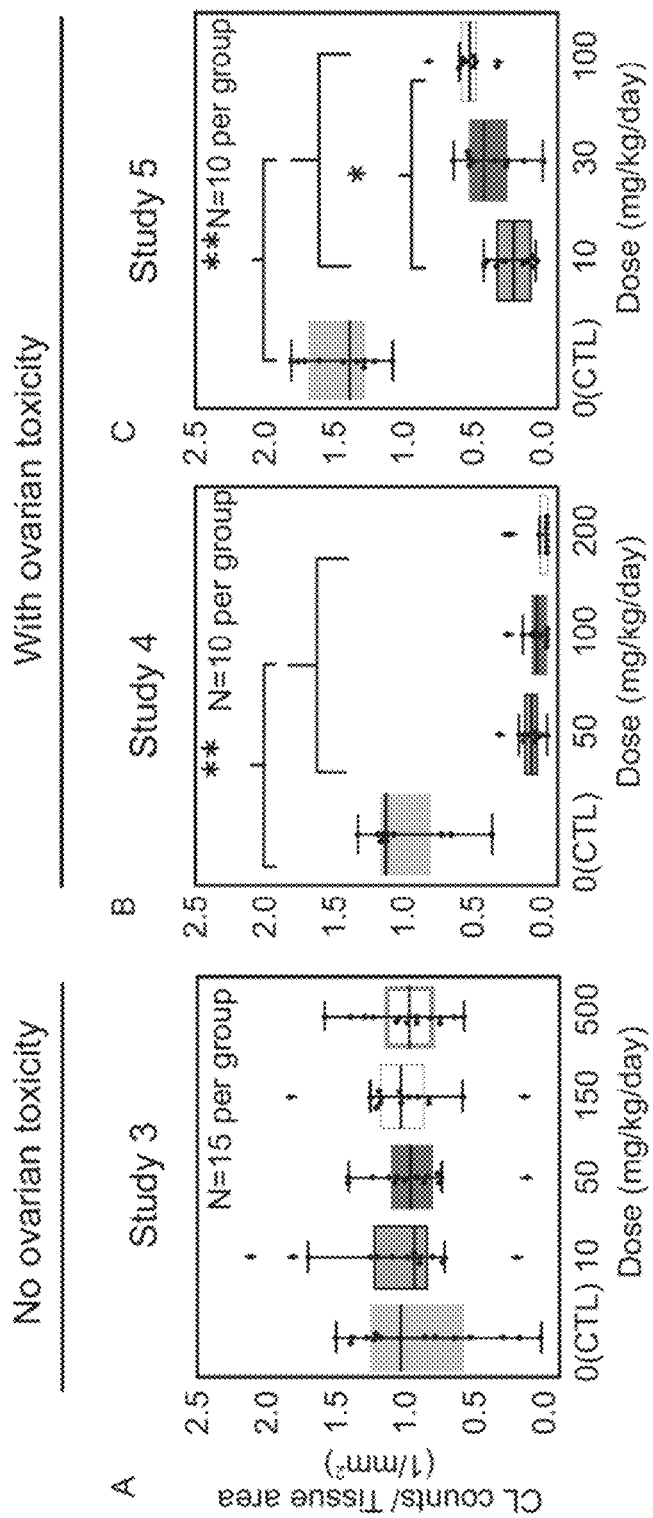
FIGS. 8A, 8B, and 8C illustrate example results indicating that tissue with ovarian toxicity demonstrated significantly lower CL count normalized to tissue area in accordance with various embodiments.

V.A.8 when Normalized to Tissue Area, Model-Generated CL Counts are Consistent with Pathologists' Study Interpretation To test the method against the pathologist's overall interpretation of the images and study conclusions, sections from two studies in which dose-dependent changes in CL counts were observed by pathologists were used in addition to the Study 3 which had ovarian toxicity findings. FIG. 8A, FIG. 8B, and FIG. 8C show the mean CL count normalized to tissue area of the rats in the control groups and in the treated groups for Studies 3, 4 and 5. No ovarian toxicity was identified for rats with compound A in Study 3, see FIG. 8A. Ovarian toxicity was identified for rats treated with compound C in Study 4, see FIG. 8B, and compound D in Study 5, see FIG. 8C. The control rats demonstrated significantly CL counts normalized to tissue area than the treated rats in both Study 4 and 5 whereas the CL counts normalized to tissue area in the control rats and the treated rats were similar. Moreover, the rats in 100 mg/kg/day dose group showed significantly CL counts normalized to tissue area than the 10 mg/kg/day dose group. P values were computed from Wilcoxon rank sum test (*: $p<0.05$, **: $p<0.01$). CL count normalized to tissue area in the control groups in Studies 4 and 5 were both significantly higher than every treated group in both studies ($p<<0.01$ when comparing the control group to any treated group) whereas no significant difference in the normalized CL count was observed in Study 3 ($p=0.27$). Interestingly in FIG. 8C, the CL count normalized to tissue area was significantly lower in the low dose group when compared to the high dose group in Study 5 ($p<0.05$).

VI. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method comprising:
   obtaining a set of images of tissue slices from one or more ovaries treated with an amount of a compound;
   inputting the set of images into a neural network model constructed as a one-stage detector using focal loss as at least a portion of the loss function;
   predicting, using the neural network model, coordinates for a bounding box around one or more objects within the set of images that are identified as corpora lutea (CL);
   outputting, using the neural network model, the set of images with the bounding box around the one or more objects that are identified as the CL based on the coordinates predicted for the bounding box;

counting the bounding boxes within the set of images output from the neural network model to obtain a CL count for the ovary; and determining an ovarian toxicity of the compound at the amount based on the CL count for the ovary, wherein the determining the ovarian toxicity comprises examining the CL count for the ovary in relation to a given condition, indicative of whether the compound at the amount is toxic to the ovary.

2. The method of claim 1, further comprising identifying, using the neural network model, the one or more objects within the set of images as being the CL, wherein the identifying comprises generating a probability score for each object of the one or more objects that is identified as the CL, and the counting comprises only counting the bounding boxes within the set of images around the one or more objects identified as the CL and having a probability score greater than a predetermined probability score threshold.

3. The method of claim 1, wherein the examining the CL count for the ovary comprises comparing the CL count for the ovary to a predetermined toxicity threshold, when the CL count is above the predetermined toxicity threshold, determining the compound at the amount is not toxic to the ovary, and when the CL count is below or equal to the predetermined toxicity threshold, determining the compound at the amount is toxic to the ovary.

4. The method of claim 1, wherein the set of images of the tissue slices are obtained from an ovary of a subject treated with the amount of the compound, and the method further comprises:

obtaining another set of images of tissue slices from another ovary of the subject treated with the amount of the compound;

generating, using the neural network model, the another set of images with a bounding box around one or more objects of objects that are identified as the CL within the another set of images based on coordinates predicted for the bounding box; and counting the bounding boxes within the another set of images output from the neural network model to obtain another CL count for the another ovary, wherein the examining the CL count for the ovary comprises:

averaging the CL count for the ovary and the another CL count for the another ovary to obtain an averaged CL count, wherein the ovarian toxicity of the compound at the amount is determined based on the average CL.

5. The method of claim 1, further comprising:

obtaining another set of images of tissue slices from one or more other ovaries that are either untreated or treated with a different amount of the compound;

generating, using the neural network model, the another set of images with a bounding box around one or more objects of objects that are identified as the CL within the another set of images based on coordinates predicted for the bounding box; and counting the bounding boxes within the another set of images output from the neural network model to obtain another CL count for the ovary, wherein the examining the CL count for the ovary comprises determining a trend between the CL count for the one or more ovaries and the another CL count for the one or more other ovaries, and the ovarian toxicity of the compound is determined at the amount or at the different amount based on the trend.

6. The method of claim 1, further comprising:

obtaining another set of images of tissue slices from one or more other ovaries that are treated with an amount of a different compound;

generating, using the neural network model, the another set of images with a bounding box around one or more objects of objects that are identified as the CL within the another set of images based on coordinates predicted for the bounding box;

counting the bounding boxes within the another set of images output from the neural network model to obtain another CL count for the ovary of the another subject; and determining an ovarian toxicity of the different compound at the amount based on the CL count for the one or more other ovaries.

7. The method of claim 1, further comprising:

providing the set of images with the bounding box around each object of the objects that is identified as the CL, the CL count for the one or more ovaries, the ovarian toxicity of the compound at the amount, or any combination thereof; and administering a treatment with the compound based on the ovarian toxicity of the compound at the amount.

8. A computer-program product tangibly embodied in a non-transitory machine-readable storage medium, including instructions configured to cause one or more data processors to perform actions including:

obtaining a set of images of tissue slices from one or more ovaries treated with an amount of a compound;

inputting the set of images into a neural network model constructed as a one-stage detector using focal loss as at least a portion of the loss function;

predicting, using the neural network model, coordinates for a bounding box around one or more objects within the set of images that are identified as corpora lutea (CL);

outputting, using the neural network model, the set of images with the bounding box around the one or more objects that are identified as the CL based on the coordinates predicted for the bounding box;

counting the bounding boxes within the set of images output from the earning neural network model to obtain a CL count for the ovary; and determining an ovarian toxicity of the compound at the amount based on the CL count for the ovary, wherein the determining the ovarian toxicity comprises examining the CL count for the ovary in relation to a given condition, indicative of whether the compound at the amount is toxic to the ovary.

9. The computer-program product of claim 8, wherein the actions further include identifying, by the neural network model, the one or more objects within the set of images as being the CL, and wherein the identifying comprises generating a probability score for each object of the one or more objects that is identified as the CL, and the counting comprises only counting the bounding boxes within the set of images around the one or more objects identified as the CL and having a probability score greater than a predetermined probability score threshold.

10. The computer-program product of claim 8, wherein the examining the CL count for the ovary comprises comparing the CL count for the ovary to a predetermined toxicity threshold, when the CL count is above the predetermined toxicity threshold, determining the compound at the amount is not toxic to the ovary, and when the CL count is below or equal to the predetermined toxicity threshold, determining the compound at the amount is toxic to the ovary.

11. The computer-program product of claim 8, wherein the set of images of the tissue slices are obtained from an ovary of a subject treated with the amount of the compound and the actions further include:
  obtaining another set of images of tissue slices from another ovary of the subject treated with the amount of the compound;
  generating, using the neural network model, the another set of images with a bounding box around one or more objects of objects that are identified as the CL within the another set of images based on coordinates predicted for the bounding box; and
  counting the bounding boxes within the another set of images output from the neural network model to obtain another CL count for the another ovary,
wherein the examining the CL count for the ovary comprises:
  averaging the CL count for the ovary and the another CL count for the another ovary to obtain an averaged CL count,
  wherein the ovarian toxicity of the compound at the amount is determined based on the average CL.

12. The computer-program product of claim 8, wherein the actions further include:
  obtaining another set of images of tissue slices from one or more other ovaries that are either untreated or treated with a different amount of the compound;
  generating, using the neural network model, the another set of images with a bounding box around one or more objects of objects that are identified as the CL within the another set of images based on coordinates predicted for the bounding box; and
  counting the bounding boxes within the another set of images output from the neural network model to obtain another CL count for the ovary,
  wherein the examining the CL count for the ovary comprises determining a trend between the CL count for the one or more ovaries and the another CL count for the one or more other ovaries, and the ovarian toxicity of the compound is determined at the amount or at the different amount based on the trend.

13. The computer-program product of claim 8, the actions further include:
  obtaining another set of images of tissue slices from one or more other ovaries that are treated with an amount of a different compound;
  generating, using the neural network model, the another set of images with a bounding box around one or more objects of objects that are identified as the CL within the another set of images based on coordinates predicted for the bounding box;
  counting the bounding boxes within the another set of images output from the neural network model to obtain another CL count for the ovary of the another subject; and
  determining an ovarian toxicity of the different compound at the amount based on the CL count for the one or more other ovaries.

14. The computer-program product of claim 8, wherein the actions further include providing the set of images with the bounding box around each object of the objects that is identified as the CL, the CL count for the one or more ovaries, the ovarian toxicity of the compound at the amount, or any combination thereof.

15. A system comprising:
  one or more data processors; and
  a non-transitory computer readable storage medium containing instructions which, when executed on the one or more data processors, cause the one or more data processors to perform actions including:
    obtaining a set of images of tissue slices from one or more ovaries treated with an amount of a compound;
    inputting the set of images into a neural network model constructed as a one-stage detector using focal loss as at least a portion of the loss function;
    predicting, using the neural network model, coordinates for a bounding box around one or more objects within the set of images that are identified as corpora lutea (CL);
    outputting, using the neural network model, the set of images with the bounding box around the one or more objects that are identified as the CL based on the coordinates predicted for the bounding box;
    counting the bounding boxes within the set of images output from the neural network model to obtain a CL count for the ovary; and
    determining an ovarian toxicity of the compound at the amount based on the CL count for the ovary, wherein the determining the ovarian toxicity comprises examining the CL count for the ovary in relation to a given condition, indicative of whether the compound at the amount is toxic to the ovary.

16. The system of claim 15, wherein the actions further include identifying, by the neural network model, the one or more objects within the set of images as being the CL, and wherein the identifying comprises generating a probability score for each object of the one or more objects that is identified as the CL, and the counting comprises only counting the bounding boxes within the set of images around the one or more objects identified as the CL and having a probability score greater than a predetermined probability score threshold.

17. The system of claim 15, wherein the examining the CL count for the ovary comprises comparing the CL count for the ovary to a predetermined toxicity threshold, when the CL count is above the predetermined toxicity threshold, determining the compound at the amount is not toxic to the ovary, and when the CL count is below or equal to the predetermined toxicity threshold, determining the compound at the amount is toxic to the ovary.

18. The system of claim 15, wherein the set of images of the tissue slices are obtained from an ovary of a subject treated with the amount of the compound, and the actions further include:
  obtaining another set of images of tissue slices from another ovary of the subject treated with the amount of the compound;
  generating, using the neural network model, the another set of images with a bounding box around one or more objects of objects that are identified as the CL within the another set of images based on coordinates predicted for the bounding box; and
  counting the bounding boxes within the another set of images output from the neural network model to obtain another CL count for the another ovary,
wherein the examining the CL count for the ovary comprises:
  averaging the CL count for the ovary and the another CL count for the another ovary to obtain an averaged CL count, wherein the ovarian toxicity of the compound at the amount is determined based on the average CL.

19. The system of claim 15, wherein the actions further include:

obtaining another set of images of tissue slices from one or more other ovaries that are either untreated or treated with a different amount of the compound;

generating, using the neural network model, the another set of images with a bounding box around one or more objects of objects that are identified as the CL within the another set of images based on coordinates predicted for the bounding box; and counting the bounding boxes within the another set of images output from the neural network model to obtain another CL count for the ovary, wherein the examining the CL count for the ovary comprises determining a trend between the CL count for the one or more ovaries and the another CL count for the ovary, and the ovarian toxicity of the compound is determined at the amount or at the different amount based on the trend.

20. The system of claim 15, the actions further include:

obtaining another set of images of tissue slices from one or more other ovaries that are treated with an amount of a different compound;

generating, using the neural network model, the another set of images with a bounding box around one or more objects of objects that are identified as the CL within the another set of images based on coordinates predicted for the bounding box;

counting the bounding boxes within the another set of images output from the neural network model to obtain another CL count for the ovary of the another subject; and determining an ovarian toxicity of the different compound at the amount based on the CL count for the one or more other ovaries.

* * * * *